(12) United States Patent
Bendfeldt

(10) Patent No.: US 10,423,893 B2
(45) Date of Patent: Sep. 24, 2019

(54) ADAPTIVE INTERFACE FOR SCREEN-BASED INTERACTIONS

(71) Applicant: Hannes Bendfeldt, Sunnyside, NY (US)

(72) Inventor: Hannes Bendfeldt, Sunnyside, NY (US)

(*) Notice: Subject to any disclaimer, the term of this patent is extended or adjusted under 35 U.S.C. 154(b) by 0 days.

(21) Appl. No.: 16/053,270

(22) Filed: Aug. 2, 2018

(65) Prior Publication Data

US 2019/0042981 A1 Feb. 7, 2019

Related U.S. Application Data

(60) Provisional application No. 62/605,179, filed on Aug. 4, 2017, provisional application No. 62/541,899, filed on Aug. 7, 2017.

(51) Int. Cl.
*G06N 20/00* (2019.01)
*G06F 9/451* (2018.01)

(52) U.S. Cl.
CPC .............. *G06N 20/00* (2019.01); *G06F 9/451* (2018.02)

(58) Field of Classification Search
CPC .... G06F 19/00; G06F 3/04842; G06F 3/0482; G06F 3/017; G06F 3/04845; G06F 3/04847; G06F 3/011; G06F 19/3481; G06F 3/0346; G06F 3/04815; G06F 3/013; G06F 3/0485; G06F 3/0481; G06F 3/167; G06F 19/3418; G06F 1/163; G06F 19/3468; G06F 1/1698; G06F 3/0488; G06F 1/1626; G06F 17/30; G06F 3/0325; G06F 3/04817; G06F 3/165; G06F 17/18; G06F 17/3053; G06F 19/326; G06F 3/012; G06F 3/014; G06F 3/0236; G06F 3/0304; G06F 3/03545; G06F 3/048; G06F 3/04812; G06F 3/0484; G06F 3/04883; G06F 3/04886; G06F 8/38; G06F 8/61; G06F 9/451; G06F 11/1469; G06F 11/3006; G06F 11/3438; G06F 13/00; G06F 15/00; G06F 17/21; G06F 17/24; G06F 17/248; G06F 17/276; G06F 17/30029; G06F 17/30256; G06F 17/30277; G06F 17/30377; G06F 17/30424; G06F 17/30477; G06F 17/30522; G06F 17/30554; G06F 17/30598; G06F 17/30837; G06F 17/30846; G06F 17/30861; G06F 17/5095;

(Continued)

(56) References Cited

U.S. PATENT DOCUMENTS

2014/0099614 A1* 4/2014 Hu .................. G09B 19/00 434/236
2014/0316305 A1* 10/2014 Venkatraman ........ A61B 5/1112 600/595

(Continued)

*Primary Examiner* — Paulinho E Smith
(74) *Attorney, Agent, or Firm* — Georgiy L. Khayet

(57) ABSTRACT

Systems and methods for customizing an output based on user data are described herein. An example method for customizing an output based on user data may commence with capturing, by at least one sensor, the user data. The method may continue with analyzing, by at least one computing resource, the user data received from the at least one sensor. The method may further include continuously customizing, by an adaptive interface, output data using at least one machine learning technique based on the analysis of the user data. The customized output data may be intended to elicit a personalized change.

20 Claims, 24 Drawing Sheets

(58) Field of Classification Search
CPC .... G06F 19/24; G06F 19/3475; G06F 1/1694;
G06F 21/31; G06F 21/32; G06F 21/629;
G06F 2201/84; G06F 2203/04105; G06F
3/016; G06F 3/02; G06F 3/0227; G06F
3/03547; G06F 3/0362; G06F 3/0487;
G06F 3/14; G06F 7/02; G06F 9/453;
G06F 9/461
See application file for complete search history.

(56) References Cited

U.S. PATENT DOCUMENTS

2017/0300186 A1* 10/2017 Kuhar ................... G06F 3/0482
2018/0070840 A1* 3/2018 Cronin ............... A61B 5/02438

* cited by examiner

ADAPTIVE INTERFACE FOR SCREEN-BASED INTERACTIONS

CROSS-REFERENCE TO RELATED APPLICATIONS

The present utility patent application is related to and claims the priority benefit under 35 U.S.C. 119(e) of U.S. provisional patent application No. 62/605,179, filed on Aug. 4, 2017, titled "Adaptive interface for screen-based interaction," and U.S. provisional patent application No. 62/541,899, filed on Aug. 7, 2017, titled "Adaptive interface with machine learning and biofeedback for screen and/or audio-based interactions. Machine learning processes sensor data, and outputs dynamic screen and audio-based interaction, e.g., graphical user interface (GUI), computer generated images (CGI), visual and/or audio environment, and user experience design (UX). Screen and/or audio work environment and interactions are modified and adapted to the data from the user using machine learning based on input from sensor." The disclosures of these related provisional applications are incorporated herein by reference for all purposes to the extent that such subject matter is not inconsistent herewith or limiting hereof.

TECHNICAL FIELD

The present disclosure relates generally to data processing and, more particularly, to customizing output data on an electronic device associated with a user based on biological data of the user.

BACKGROUND

Conventionally, people use digital devices, such as smartphones, tablets, and laptops, in many environments with different lighting conditions, e.g., indoors in daylight, indoors in artificial light, outdoors in clear weather, outdoors in cloudy weather, and the like. The digital devices may be configured to automatically adjust display parameters to suit the environmental conditions and the content a user is currently viewing. In other words, a digital device may have 'an adaptive display' feature that may enable the digital device to automatically adjust a color range, contrast, and sharpness of a display according to the current usage of the digital device by the user. The digital device may sense the environmental conditions, determine the type of content the user is viewing, determine a particular application the user is using, and analyze all collected data to select parameters for optimizing the viewing experience of the user.

Additionally, according to scientific studies, exposure to blue light of the visible light spectrum was found to have an impact on health of a person by contributing to eye strain. Blue light also was determined to be important in regulating sleep/wake cycles of a body of the person. The display screens of smartphones, computers, laptops, and other digital devices are sources of significant amounts of blue light. Therefore, some conventional digital devices are configured to adapt the color range of a display by activating blue light filtering at night or at time intervals selected by the user to reduce amounts of blue light emitted by the screens.

However, although displays of digital devices can be adjusted based on particular environmental parameters collected by the digital devices and current settings of the digital devices, conventional digital devices do not analyze the current physiological state of the user when adjusting the parameters of the display. Therefore, the adjusted parameters of the digital device may be irrelevant to physiological parameters of the user.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are computer-implemented systems and methods for customizing output based on user data. In some example embodiments, a machine learning system for customizing output based on user data may include at least one sensor, at least one computing resource, and an adaptive interface. The at least one sensor may be configured to capture the user data. The at least one computing resource may be configured to analyze the user data received from the at least one sensor. The adaptive interface may be configured to continuously customize output data using at least one machine learning technique based on the analysis of the user data. The customized output data may be intended to elicit a personalized change.

In some example embodiments, a method for customizing an output based on user data may commence with capturing, by at least one sensor, the user data. The method may continue with analyzing, by at least one computing resource, the user data received from the at least one sensor. The method may further include continuously customizing, by an adaptive interface, output data using at least one machine learning technique based on the analysis of the user data. The customized output data may be intended to elicit a personalized change.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and, in which.

DETAILED DESCRIPTION

Figure 1:
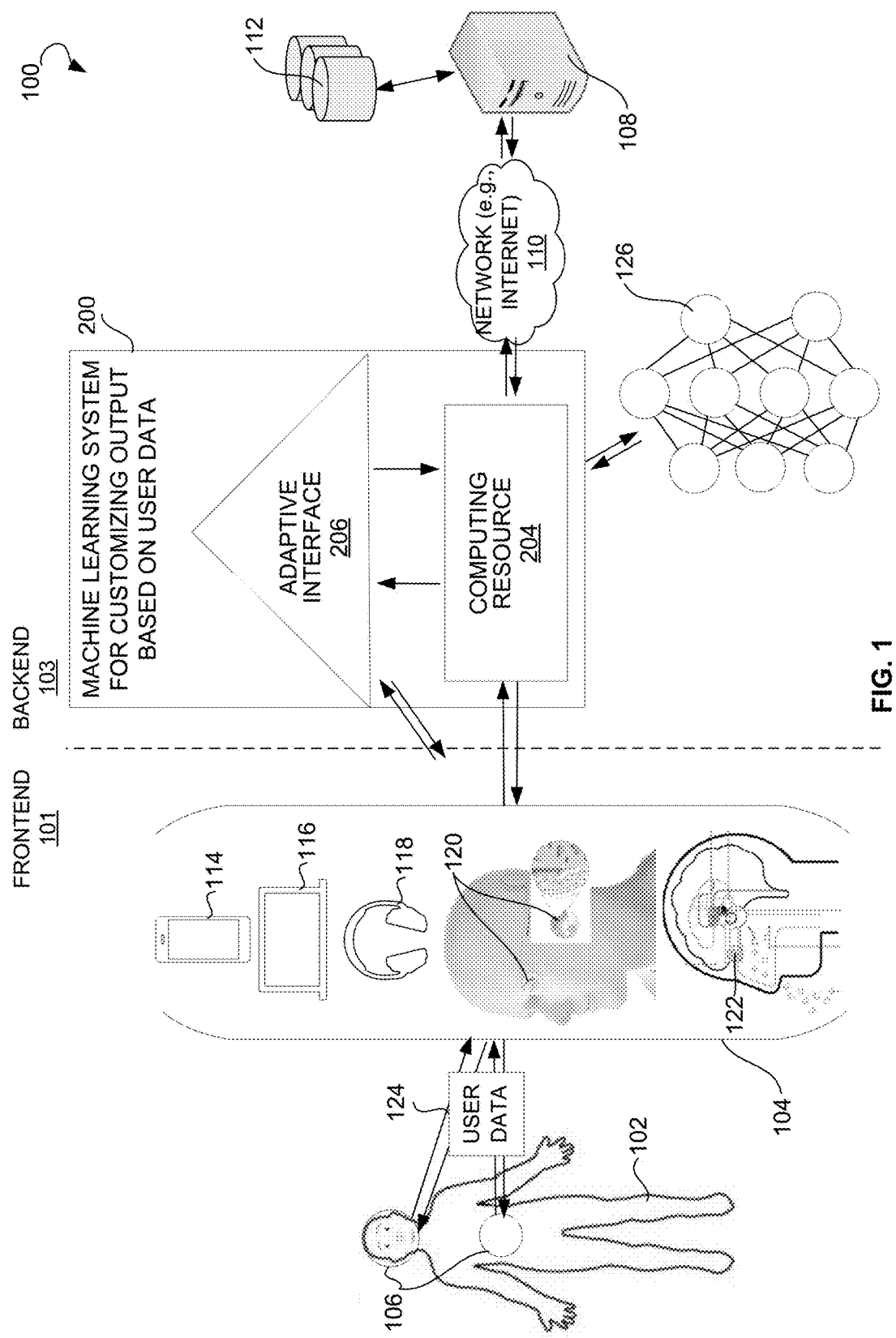
FIG. 1 illustrates an environment within which systems and methods for customizing output based on user data can be implemented, in accordance with some embodiments.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure provides methods and systems for customizing output based on user data. The system for customizing output based on user data of the present disclosure may continuously customize an output provided by a digital device associated with a user to elicit a personalized change of biological parameters of the user. Specifically, the system may collect user data, such as biological data of the user or other users, historical data of the user or other users, ambient data, and the like. The biological data may include data related to physical parameters of the user, e.g., a heart rate, body temperature, a blood oxidation level, presence of a substance in a blood, a blood glucose level, and the like. The user data may be collected by sensors affixed to the user, such as a heart-rate monitor; sensor located in proximity to the user, such as a thermal imaging camera and a digital camera; sensors embedded into the digital device of the user; and the like. The system may analyze the collected user data.

The system includes an adaptive interface unit, also referred herein to as an adaptive interface, that uses the results of the analysis to continuously customize output data on the digital device of the user, also referred to herein as a user device. The adaptive interface applies machine learning techniques to process the results of analysis of the collected user data and select changes to a graphics output and/or an audio output on the user device to cause the change in biological data of the user. Specifically, the adaptive interface may continuously analyze the relationship between the biological data of the user, such as a heart rate, and the graphics and audio the user experiences when using the digital device. The results of continuous analysis of dependencies between the biological data of the user and the output data provided to the user on the user device may be stored in a database in a form of historic data associated with the user. Additionally, data on dependencies between biological data of a plurality of users and output data on digital devices of the plurality of users may be stored in the database (for example, in a form of historic data associated with the plurality of users).

Therefore, the adaptive interface may determine, based on the analysis of the collected user data, that the user has an increased heart rate at the current moment of time, and adapt the output data on the interface of the digital device to elicit reduction of the heart rate of the user. For example, the adaptive interface may determine, based on the historic data, that the heart rate of the user typically changes in response to change of the volume of the audio output and brightness of the video output. Based on such determination, the adaptive interface may reduce the volume of the audio output and decrease the brightness of a display of the user device to cause the reduction of the heart rate of the user.

Thus, the adaptive interface may relate to bio-adaptive technology and may perform the adaptation of an output of the user device based on biological parameters of the user. The adaptation of the output of the user device may be directed to eliciting the change of the biological parameters of the user in case the biological parameters of the user do not correspond to predetermined ranges or values.

FIG. 1 illustrates an environment 100 within which systems and methods for customizing output based on user data can be implemented, in accordance with some embodiments. The environment 100 may include a frontend 101 and a backend 103. The frontend 101 may include a sensor 106 and a user device 104 associated with a user 102. The backend 103 may include a machine learning system 200 for customizing output based on user data (also referred to as a system 200), a server 108, a data network shown as a network 110 (e.g., the Internet or a computing cloud), and a database 112. The user device 104, the system 200, the server 108, the sensor 106, and the database 112 may be connected via the network 110.

The user 102 may be associated with the user device 104. The user device 104 may include a smartphone 114, a laptop 116, headphones 118, a retinal implant 120, an artificial olfaction device 122, and so forth. In an example embodiment, the artificial olfaction device 122 may include an electronic system operating as an electronic nose of the user 102.

The network 110 may include a computing cloud, the Internet, or any other network capable of communicating data between devices. Suitable networks may include or interface with any one or more of, for instance, a local intranet, a corporate data network, a data center network, a home data network, a Personal Area Network, a Local Area Network (LAN), a Wide Area Network (WAN), a Metropolitan Area Network, a virtual private network, a storage area network, a frame relay connection, an Advanced Intelligent Network connection, a synchronous optical network connection, a digital T1, T3, E1 or E3 line, Digital Data Service connection, Digital Subscriber Line connection, an Ethernet connection, an Integrated Services Digital Network line, a dial-up port such as a V.90, V.34 or V.34bis analog modem connection, a cable modem, an Asynchronous Transfer Mode connection, or a Fiber Distributed Data Interface or Copper Distributed Data Interface connection. Furthermore, communications may also include links to any of a variety of wireless networks, including Wireless Application Protocol, General Packet Radio Service, Global System for Mobile Communication, Code Division Multiple Access or Time Division Multiple Access, cellular phone networks, Global Positioning System, cellular digital packet data, Research in Motion, Limited duplex paging network, Bluetooth radio, or an IEEE 802.11-based radio frequency network. The data network can further include or interface with any one or more of a Recommended Standard 232 (RS-232) serial connection, an IEEE-1394 (FireWire) connection, a Fiber Channel connection, an IrDA (infrared) port, a Small Computer Systems Interface connection, a Universal Serial Bus (USB) connection or other wired or wireless, digital or analog interface or connection, mesh or Digi® networking.

The sensor 106 may be affixed to any body part of the user 102. Alternatively, the sensor 106 may be located in proximity to the user 102. In a further example embodiment, the sensor 106 may be integrated into the user device 104. The sensor 106 may include a biological sensor (e.g., a heart-rate monitor), a thermal imaging camera, a breath sensor, a radar sensor, and the like. The sensor 106 may collect user data 124 and provide the collected user data 124 to the user device 104. The user device 104 may provide the user data 124 to the system 200.

The system 200 may be running on the user device 104 or in the computing cloud. The system 200 may have an access to output data reproduced by the user device 104, such as graphics and audio. The system 200 may include a computing resource 204 and an adaptive interface 206. The computing resource 204 of the system 200 may analyze the user data 124. The adaptive interface 206 may apply machine learning techniques 126 to the results of the analysis to customize the output data of the user device 104 so as to cause changing of the biological data of the user 102. In an example embodiment, the adaptive interface 206 may include a combination of sensors, machine learning algorithms, processing units, and computing resources. The adaptive interface 206 may reside in the user device 104 or remotely to the user device, e.g., in the computing cloud.

The adaptive interface 206 may also send the data obtained based on processing of the user data using machine learning algorithms to the server 108 to update the data of an application running on the user device 102. The server 108 can include at least one controller and/or at least one processor. An alternate implementation of the server 108 can include an application or software running on the user device 104. The server 108 can update and improve code associated with the application using data associated with the plurality of individual users. The server 108 can then send the updated output data associated with the application to the adaptive interface 106 via the network 110 for further displaying on the user device 104.

Figure 2:
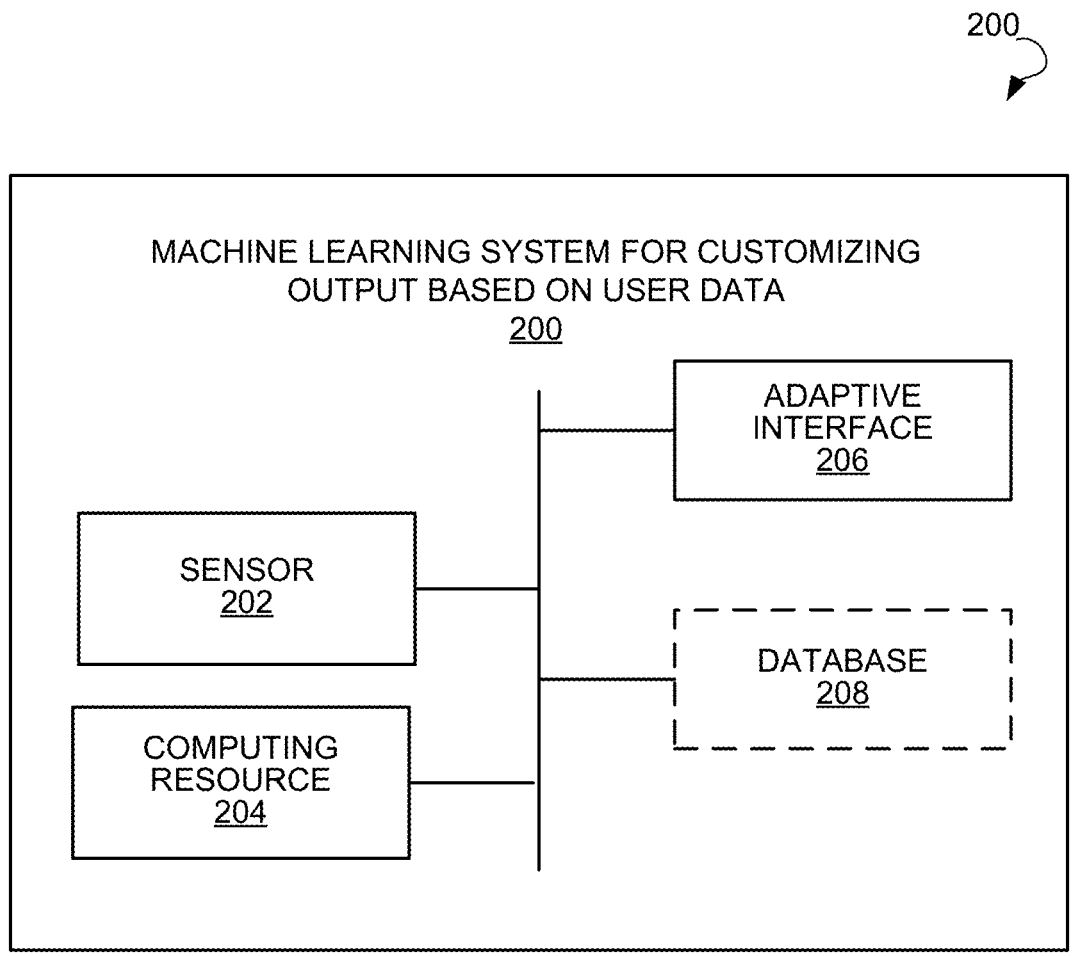
FIG. 2 is a block diagram showing various modules of a machine learning system for customizing output based on user data, in accordance with certain embodiments.

FIG. 2 is a block diagram showing various modules of a machine learning system 200 for customizing output based on user data, in accordance with certain embodiments. The system 200 may include at least one sensor shown as sensor 202, at least one computing resource shown as a computing resource 204, an adaptive interface unit shown as an adaptive interface 206, and optionally a database 208. The database 208 may include computer-readable instructions for execution by the computing resource 204 and the adaptive interface 206. In an example embodiment, each of the computing resource 204 and the adaptive interface 206 may be implemented as one or more processors. The processor may include a programmable processor, such as a microcontroller, a central processing unit (CPU), and so forth. In other embodiments, the processor may include an application-specific integrated circuit or programmable logic array, such as a field programmable gate array, designed to implement the functions performed by the system 200. In various embodiments, the system 200 may be installed on a user device or may be provided as a cloud service residing in a cloud storage.

The sensor 202 may be affixed to a user, integrated into the user device, or located in proximity to the user. The sensor 202 may include at least one of the following: a thermal imaging camera, a digital camera, a breath sensor, a depth sensor, a radar sensor, a gyroscope, and so forth. In an example embodiment, the sensor 202 may include a biological sensor. The sensor 202 may be configured to capture the user data. The user data may include at least one of the following: biological data of a user, biological data of a plurality of users, historical data of the user, historical data of the plurality of users, ambient data, and so forth. The biological data may include at least one of the following: a respiratory rate, a heart rate, a heart rate variability, an electroencephalography, an electrocardiography, an electromyography, an electrodermal activity, a mechanomyography, a haptic interaction, a motion, a gesture, pupil movement, a biological analyte, a biological structure, a microorganism, a color of skin of the user, a blood glucose level, blood oxygenation, blood pressure, and so forth. The ambient data may be associated with at least one of the following: light, heat, motion, moisture, pressure, and so forth.

The computing resource 204 may be configured to analyze the user data received from the sensor 202. The computing resource 204 may include at least one of the following: an application programming interface (API), a server, a cloud computing resource, a database, a network, a blockchain, and so forth. In an example embodiment, the at least one computing resource that may be implemented as the user device associated with the user may include one of the following: a smartphone, a tablet computer, a phablet computer, a laptop computer, a desktop computer, an augmented reality device, a virtual reality device, a mixed reality device, a retinal implant, an artificial olfaction device, headphones, an audio output device, and so forth. In a further example embodiment, the computing resource 204 may include one of a CPU, a graphics processing unit (GPU), and a neural processing unit (NPU).

The adaptive interface 206 may be configured to continuously customize output data of the user device using at least one machine learning technique based on the analysis of the user data. The at least one machine learning technique may include one or more of the following: an artificial neural network, a convolutional neural network, a Bayesian neural network, a supervised machine learning algorithm, a semi-supervised machine learning algorithm, an unsupervised machine learning algorithm, a reinforcement learning, a deep learning (ok to add?) and so forth.

The customized output data may be intended to elicit a personalized change. The personalized change may include a change in the biological data of the user. The personalized change in the user data may include at least one of the following: a change of perception time, a change of a respiratory rate, a change of a breathing rate, a change of a heart rate, a change of a heart rate variability, a change of a haptic interaction, a change of an electroencephalographic signal, a change of an electrocardiographic signal, a change of an electromyographic signal, a change of a mechanomyographic signal, a change of an electrodermal activity, a change of a motion, a change of a gesture, a change of a pupil movement, a change of a biological structure, a change of a microorganism, a change of a color of skin of the user, a change of blood glucose levels, a change of a blood oxygenation, a change of a blood pressure, a change of a biological analyte, a change of a stress level, and so forth.

The customized output data may be associated with the user device of the user, such as a smartphone, a laptop, a retinal implant, and so forth. The customized output data may include an audio output and/or a graphics output.

Figure 3:
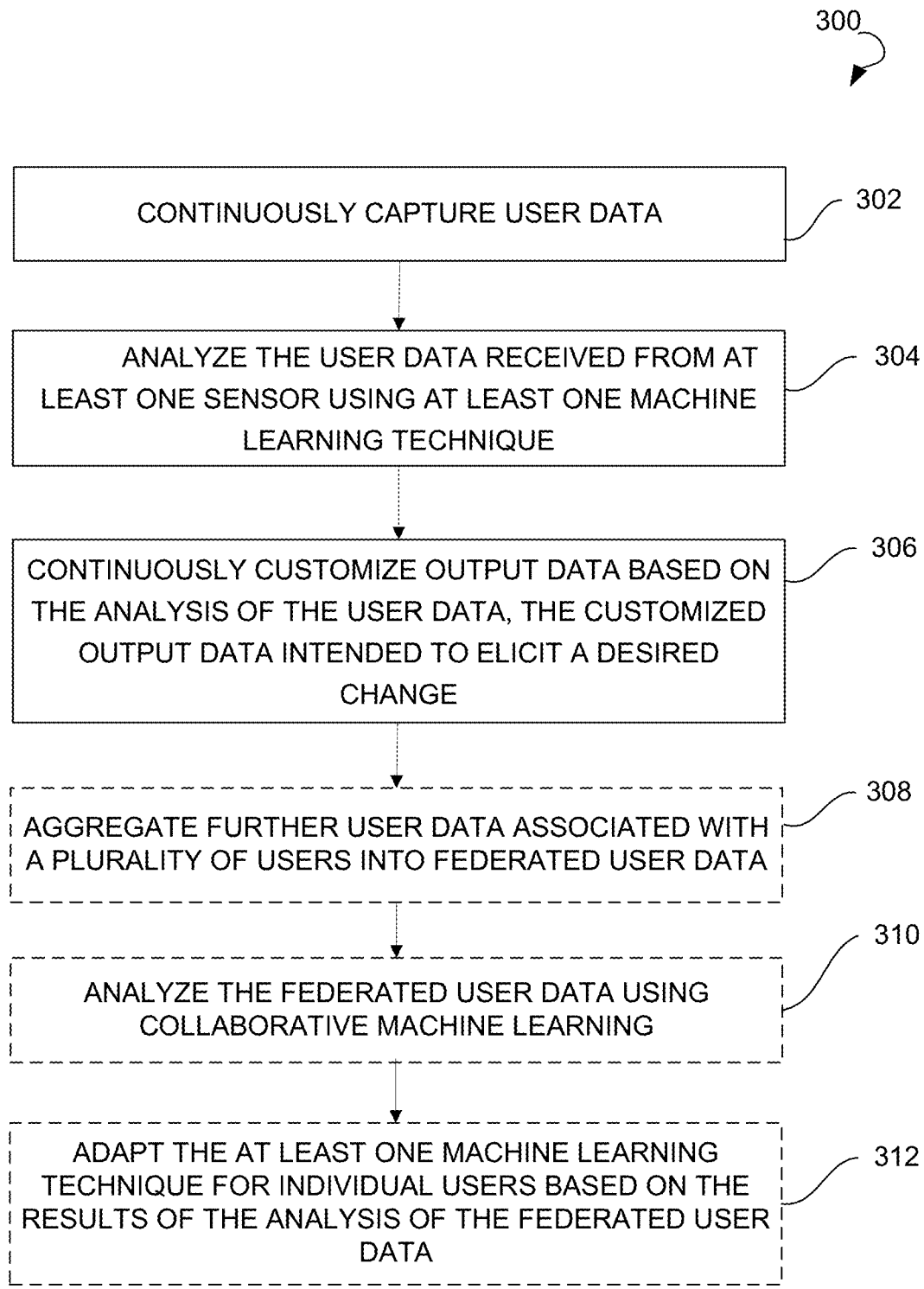
FIG. 3 is a flow chart illustrating a method for customizing output based on user data, in accordance with some example embodiments.

FIG. 3 is a flow chart illustrating a method 300 for customizing an output based on user data, in accordance with some example embodiments. In some embodiments, the operations may be combined, performed in parallel, or performed in a different order. The method 300 may also include additional or fewer operations than those illustrated. The method 300 may be performed by processing logic that may comprise hardware (e.g., decision making logic, dedicated logic, programmable logic, and microcode), software (such as software run on a general-purpose computer system or a dedicated machine), or a combination of both.

The method 300 may commence at operation 302 with capturing, by at least one sensor, the user data. The sensor may be configured to continuously capture the user data in real-time (e.g., when the user is awake and asleep), capture the user data during the usage of the user device by the user, or capture the user data at predetermined times. The at least one sensor may include a thermal imaging camera, a digital camera, a breath sensor, a depth sensor, a radar sensor, a gyroscope, a thermal imaging camera, and so forth. In an example embodiment, the at least one sensor may include a device for analyzing electronic signals emitted by a user. The method 300 may further include extracting, by the device for analyzing electronic signals, one of a physiological parameter of the user and an activity associated with the user.

The method 300 may continue at operation 304 with analyzing, by at least one computing resource, the user data received from the at least one sensor. At operation 306, the method 300 may further include continuously customizing, by an adaptive interface, output data using at least one machine learning technique based on the analysis of the user data. The customized output data may be intended to elicit a personalized change. The personalized change may include a change of biological parameters of the user. In an example embodiment, the continuous customizing of the output data may include at least one of the following: changing a color, playing audio-perceived stimuli, providing a haptic feedback, changing a font, changing a shape of the font, changing a brightness, changing a contrast, changing an illuminance (e.g., changing values of lux of light), changing warmth, changing a saturation, changing a fade, changing a shadow, changing a sharpness, changing a structure, generating computer images, changing a tone, changing a bass, changing a volume, changing a pitch of a sound, changing a treble, changing a balance, changing a GUI, changing a UX, and so forth.

The method 300 may optionally include an operation 308, at which the at least one computing resource may aggregate further user data associated with a plurality of users into federated user data. At optional operation 310, the at least one computing resource may analyze the federated user data using collaborative machine learning. The method 300 may further include adapting, by the at least one computing resource, the at least one machine learning technique for individual users based on the results of the analysis of the federated user data at optional operation 312. In an example embodiment, the method 300 may further include continuously adapting, by the adaptive interface, a media output based on user interactions with the adaptive interface.

Figure 4:
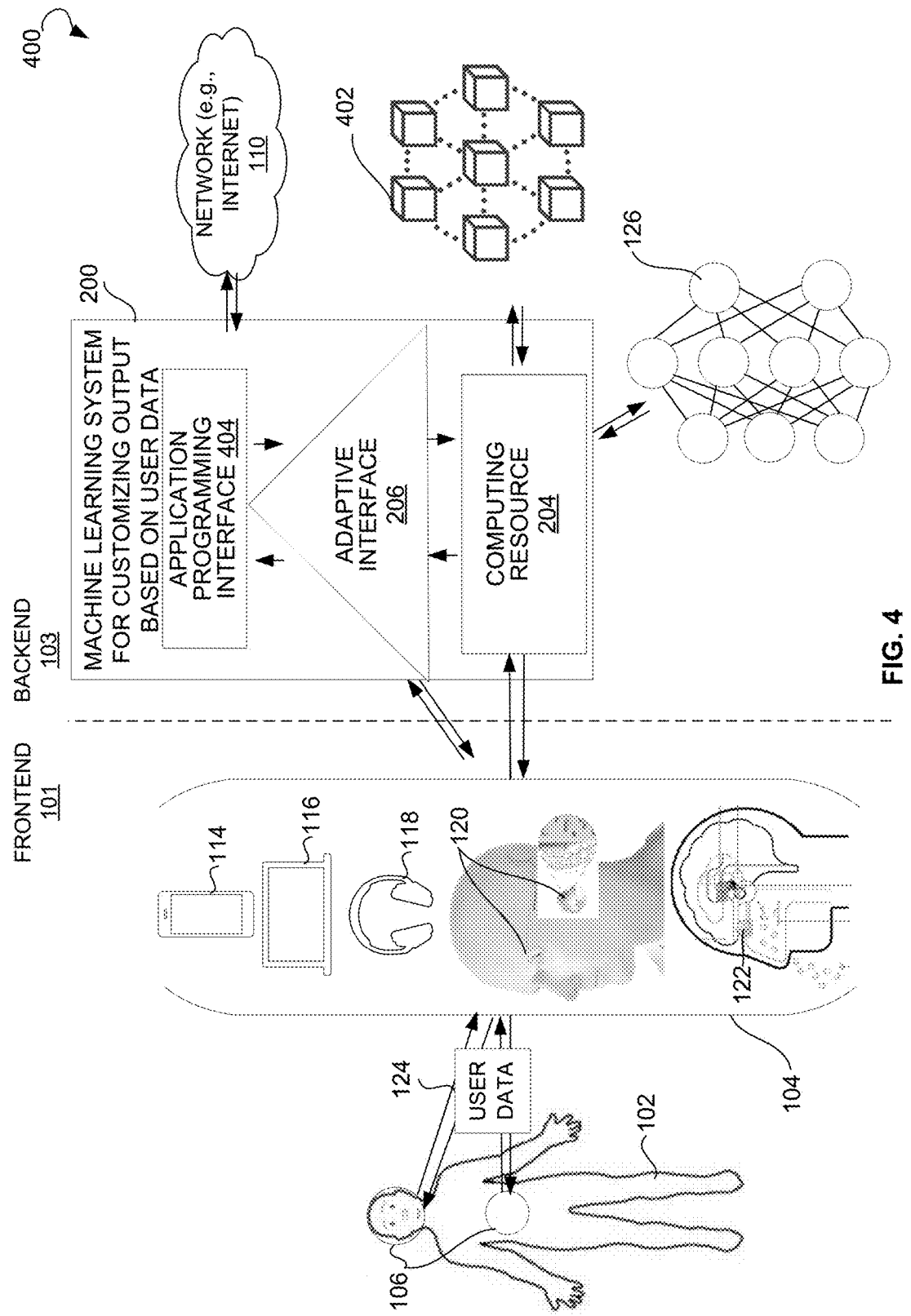
FIG. 4 illustrates a further example environment within which systems and methods for customizing an output based on user data may be implemented, in accordance with some example embodiments.

FIG. 4 illustrates a further example environment 400 in which systems and methods for customizing an output based on user data may be implemented, according to an example embodiment. The environment 400 includes a client side, shown as a frontend 101, and a backend 103. The frontend 101 can include a sensor 106 and a user device 104. The backend 103 can include a system 200, machine learning techniques 126, and a blockchain 402. The system 200 may include an API 404 to communicate with the user device 104, an adaptive interface 206, and a computing resource 204. The user device 104 may include a smartphone 114, a laptop 116, headphones 118, a retinal implant 120, and an artificial olfaction device 122, as well as a tablet computer, a phablet computer, a desktop computer, an augmented reality device, a virtual reality device, a mixed reality device, an audio output device, and so forth.

The sensor 106 can detect biological data of the user 102. Though two sensors 106 are shown on FIG. 4, any number of sensors, e.g., one, two, or more, may be attached to the user 102, integrated into the user device 104, or located in proximity to the user 102. In an example embodiment, the sensor 106 may detect a number of breaths per minute of the user 102. In other example embodiments, the sensor 106 may detect any other biological activity of the user 102, such as a heart rate, heart rate variability, electroencephalography, electromyography, mechanomyography, and so forth. In further example embodiment, the sensor 106 may be a device that analyzes electronic signals emitted by the user 102, i.e., frequencies emitted by a body of the user 102, and depicts the analyzed electronic signals as a biometric parameter or activity of the user 102. In an example embodiment, the sensor 106 can be a thermal imaging camera. The adaptive interface 206 may use deep learning algorithms of machine learning techniques 126 to analyze the heart rate and breathing rates of the user 102 based on data collected by the thermal imaging camera.

The sensor 106 may act as a passive sensor or an active sensor. When acting as a passive sensor, the sensor 106 may sense data emitted by the user 102, such as emitted thermal wavelengths. The thermal wavelengths may be analyzed by the adaptive interface 206 using deep learning algorithms of machine learning techniques 126 to determine a breathing pattern or a heart rate of the user 102. When acting as an active sensor, the sensor 106 may send towards the user 102 and receive back ultrasound or radar waves. The waves received upon being reflected from the body of the user 102 can be analyzed by the sensor 106 to detect the physiological state of the user 102.

The API 404 may include a Representational State Transfer (REST) API, 0 API, a set of subroutine definitions, protocols, and tools for receiving data from a server (such as a server 108 shown on FIG. 1). The API 404 may provide graphics and audio on the user device 104 based on data received from the adaptive interface 206. The API 404 may be associated with one or more of the following: a web-based system, an operating system, a database system, a computer hardware, and so forth.

The adaptive interface 206 may apply machine learning techniques 126 including artificial neural network, convolutional neural network, Bayesian neural network, or other machine learning techniques to enable the automatic feature learning, the machine learning inference process, and deep learning training of the adaptive interface 206. The adaptive interface 206 may receive data from the sensor 106, the user device 104, the API 404, a computing resource 204, and the network 110. In an example embodiment, the computing resource 204 may be implemented as a component of the user device 104. In this embodiment, the adaptive interface 206 may communicate with and transfer data to the user device 104 for data processing to use the processing units such as a GPU and CPU in the user device 104, and may apply predictive modeling and machine learning processes.

The machine learning techniques 126 applied by the adaptive interface 206 may include supervised machine learning, semi-supervised machine learning, unsupervised machine learning, federated machine learning, collaborative machine learning, and so forth. The supervised machine learning in the adaptive interface 206 is based on a training dataset with labeled data, already installed in the adaptive interface 206 and/or sent from the API 404 and/or network 110. For the supervised machine learning in the adaptive interface 206, the data are labeled and the algorithms learn to predict the output from the input data, namely user data 124.

The semi-supervised learning in the adaptive interface 206 uses a large amount of user data 124, data of the user device 104, and/or API 404, and only some of preinstalled data and/or data from network 110 by using a mixture of supervised and unsupervised machine learning techniques.

For unsupervised machine learning in the adaptive interface 122, all data are unlabeled and the algorithms learn to inherit structure from the user data 124, data of the user device 104, and/or API 404.

For the federated machine learning and collaborative machine learning, the adaptive interface 206 collaboratively learns a shared prediction model while keeping all the training data on the user device 104 and sensor 106, decoupling the ability to do machine learning from the need to store the data in the network 110. This goes beyond the use of local models that make predictions on computing devices by bringing model training to the computing device as well. The user device 104 downloads the current model, improves it via adaptive interface 206 by learning from user data 124 related to the interaction of the user 102 with the user device 104 and user data 124 received from the sensor 106, and then summarizes the changes as a small focused update. Only this update to the model is sent to the cloud, using encrypted communication, where it is immediately averaged with other user updates to improve the shared model. All the training data remain on the user device 104 and adaptive interface 206, and no individual updates are stored in the cloud. For the federated and collaborative machine learning setting, the data is distributed across millions of devices in a highly uneven fashion. In addition, these devices have significantly higher-latency and lower-throughput connections and are only intermittently available for training.

The user data from the sensor 106 related to biological parameters of the user 102 and user interaction with the user device 104 can be communicated to the network 110 in all machine learning models, but can also remain as personalized and customized data sets in the adaptive interface 206 and user device 104.

The adaptive interface 206 learns about the specifications for routines, data structures, object classes, variables and programming of APIs, and computing resource 204, network 110, user device 104, and sensor 106. The adaptive interface 206 processes data about the user interaction with an application running on the user device 104, such as graphics and audio from the user device 104, and the user data 124, such as biological data, from the sensor 106. The adaptive interface 206 learns how the biometric data and activity data of the user 102 are changing in real-time when the user 102 interacts with the user device 104. The adaptive interface 206 dynamically customizes the output data from API 404 using the machine learning techniques 126, and sends the customized output data back to the API 404. The API 404 sends the adapted and customized output data in real-time to the user device 104. The adaptive interface 206 may also collect data associated with the user 102 over time by receiving the biological data of the user 102 and/or data on interaction of the user 102 with the user device 104 and analyzes the collected data using deep learning techniques or other trained learning techniques. The results of the analysis of the adaptive interface 206 and the biological data of the user 102 can be processed and applied to the output data of the API 404 and the usage of the output data of the API 404 in the user device 104 to customize the graphics and audio provided on the user device 104 to the user 102.

The adaptive interface 206 can customize the output data based on the biological data of the user 102 (for example, for faster perception time of the graphics and audio in the user device 104 by the user 102). The adaptive interface 206 can also customize the graphics and audio to the physiological state of the user 102 detected and analyzed based on the biological data of the user 102. For example, a heart rate may be sensed by the sensor 106, and the adaptive interface 206 may customize the graphics and audio on the user device 104 to decrease or increase the heart rate of the user 102 in real-time while the uses interacts with the user device 104.

If the sensor 106 is a breathing sensor, the adaptive interface 206 may employ thermal imaging and machine learning techniques to adapt and customize the graphics and audio to elicit slower or longer inhales and exhales.

The adaptive interface 206 may also send the data of the machine learning to the network 110. The network 110 can send the data to the server 108 to update the data of the application running on the user device 104. The server 108 can update and improve a code associated with the application with data associated with the plurality of individual users. The server 108 can then send the updated output data to the adaptive interface 106 via the network 110.

The adaptive interface 206 can also interact with code storing networks such as blockchain 402 or cloud computing (not shown) as alternate implementations of the server 108 shown on FIG. 1. The adaptive interface 206 may send the data of the machine learning to the blockchain 402 for further processing.

In addition to the benefits of APIs, such as scalability, heterogeneous interoperability, independent evolution of client and server, and empowered clients, the adaptive interface 206 may also add customization and adaption of the output data in the user device 104 via the user data 124 of the user 102. The customization and adaption of the adaptive interface 206 can enable faster processing speeds for user interaction with the application state (graphics, UX, GUI, and audio) as in the user device 104. The adaptive interface 206 can also add stress-reduction and changes of personal biological data via the adapted and customized output data in the user device 104. The adaptive interface 206 can also improve the network speed between adaptive interface 206, API 404, and user 102 via customized and adapted information processing. The adaptive interface 206 may use different types of machine learning techniques to achieve smarter models, lower latency, and less power consumption to potentially ensure privacy when data of user 102 remain on the user device 104 and in adaptive interface 206. This approach has another immediate benefit: in addition to providing an update to the shared model to the network 110 and customized output data, the improved and updated output data on the user device 104 can also be used immediately in real-time to provide user experience personalized based on the way the user 102 uses the user device 104. The adaptive interface 206 can also replace the API 404 with the API generated based on the output data. The adaptive interface 206 can feature all the programming tasks and steps employed in API and replace the API by connecting sensors, user devices, and networks for customized and improved applications, performances, and experiences.

Figure 5:
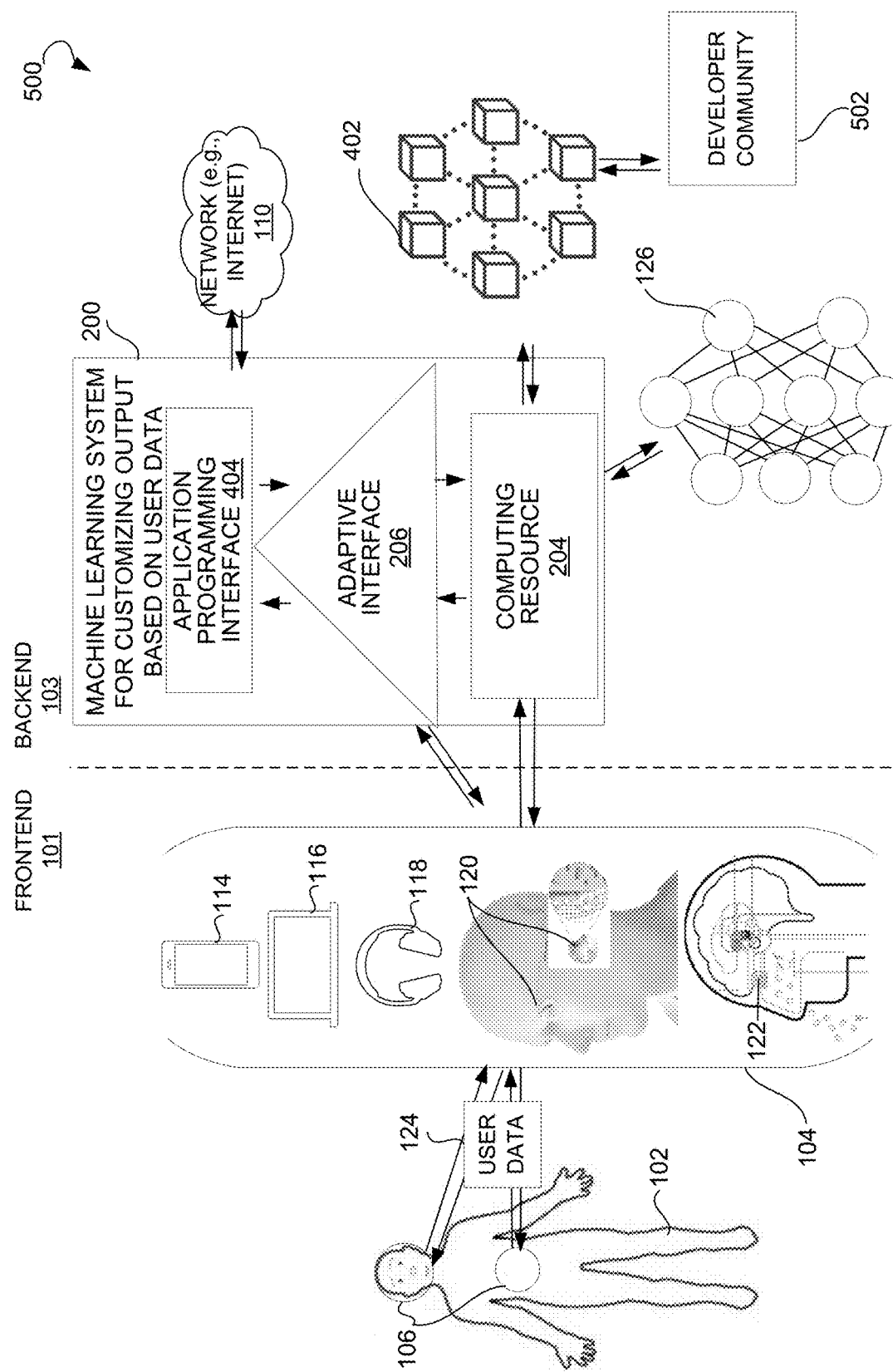
FIG. 5 illustrates a further environment within which systems and methods for customizing output based on user data can be implemented, in accordance with some example embodiments.

FIG. 5 illustrates an environment 500 within which systems and methods for customizing output based on user data can be implemented, in accordance with some embodiments. The system 200 may be in communication with the blockchain 402 and provide the user data 124 to the blockchain 402. The blockchain 402 may be in communication with a developer community 502 and may provide results of analysis of the user data 124 to the developer community 502. The developer community 502 may use the analysis of the user data 124 to develop further machine learning models for processing the user data 124 by the blockchain 402.

Figure 6:
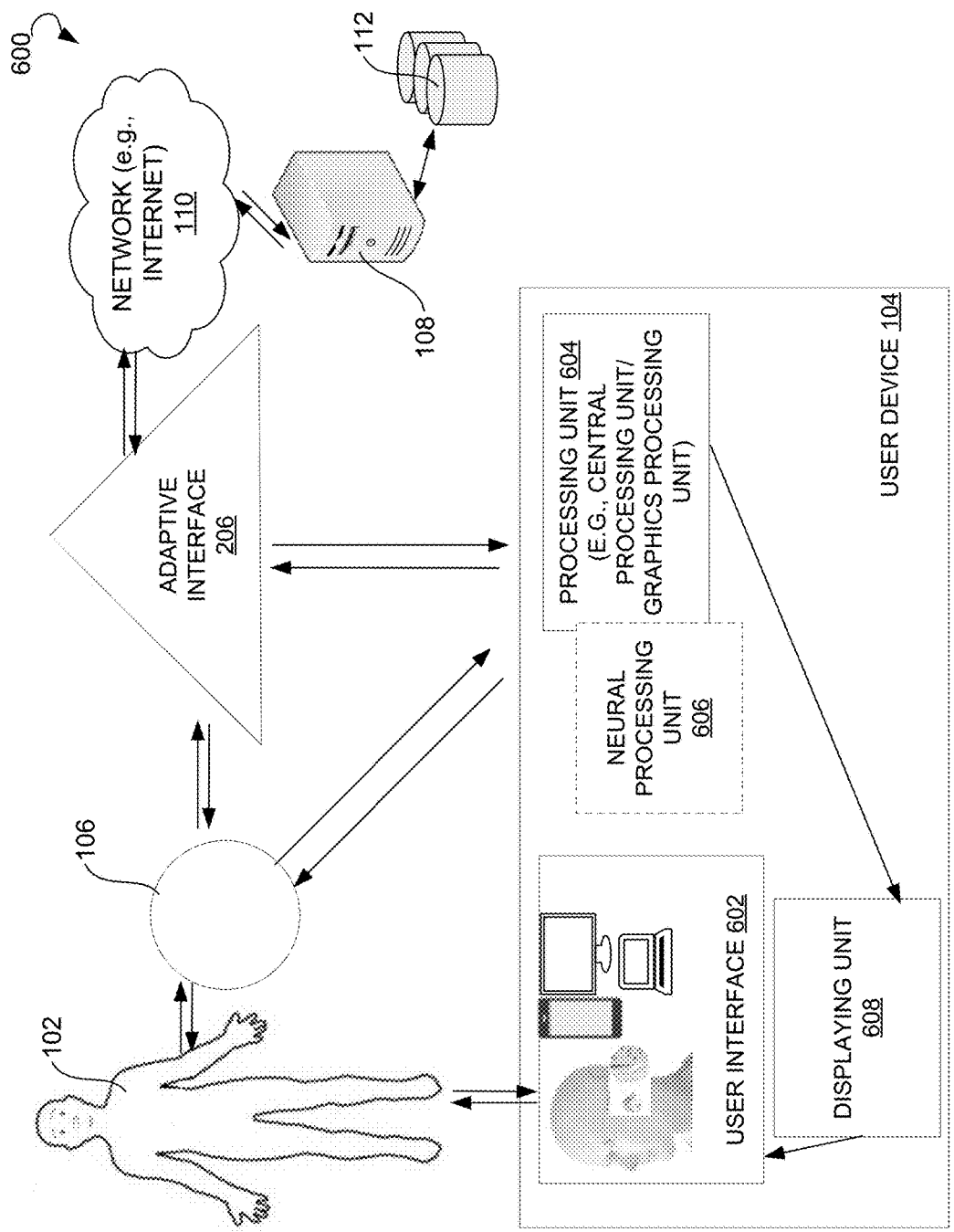
FIG. 6 is a schematic diagram that illustrates operations performed by components of a machine learning system for customizing output based on user data, in accordance with some example embodiments.

FIG. 6 is a schematic diagram 600 that illustrates operations performed by components of a machine learning system for customizing output based on user data, according to an example embodiment. The user device 104 may display graphics and play audio to a user 102. The user device 104 may include a user interface 602, a processing unit 604, an NPU 606, and a displaying unit 608. An adaptive interface 206 of the machine learning system 200 for customizing output based on user data may be located remotely with respect to the user device 104 (e.g., in a computing cloud). In an example embodiment, the NPU 606 may be not the component of the user device 104, but may be located remotely with respect to the user device 104 (e.g., in the computing cloud).

The user 102 may perceive the output in a form of visual data and/or audio data provided by the user device 104 via the user interface 602, UX, CGI, common gateway interface, a work environment (e.g., a social media platform), and other forms of graphics and potential audio files or audio-perceived frequencies. In an example embodiment, a screen of the user device 104 may display visually-perceived stimuli, for instance, when the user 104 device uses a retinal implant technology. The user device 104 can be configured in a form of a computing and processing unit and may be further configured to provide visual stimuli and play audio-perceived stimuli.

The user 102 may interact with the user device 104. The interaction can be in any manner, for example, by perceiving, visually or audibly, an application running on the user device 104, by changing the visuals or audio on the user device 104, for example, by haptically interacting with the user device 104. The user 102 can interact with the user device 104 by pressing buttons displayed on the user interface 602 of the user device 104 with fingers. In a further example embodiment, pupil movements of the user 102 or other forms of interaction of the user 102 may be tracked.

A sensor 106 may be affixed to the user 102 or may be located in proximity to the user 102 and may sense data related to physical parameters of the user 102 and convert the data into an electrical signal. The sensed data may be considered to be an input from the user 102. The input may include light, heat, motion, moisture, pressure, or any other physical parameters of the body of the user 102 that can be sensed by the sensor 106. The sensor 106 that detects changes of the physical parameters of the user 102 may be a biosensor configured to detect the presence or concentration of a biological analyte, such as a biomolecule, a biological structure, or a microorganism in/at the body of the user 102. The sensor 106 in a form of the biosensor may include three parts: a component that recognizes the analyte and produces a signal, a signal transducer, and a reader device. The sensor 106 may provide an output in a form of a signal that may be transmitted electronically to the adaptive interface 206 for reading and further processing.

The sensor 106 may further be a camera configured to detect changes of physical parameters of the user 102, such as the color of the skin of the user 102. The images can be analyzed using machine learning algorithms, e.g., using the NPU 606 or the adaptive interface 206, to evaluate the changes of biological parameters of the user 102 (for example, a heart rate of the user 102). Some types of the sensor 106 may require the use of learning algorithms and machine learning techniques in the adaptive interface 206, the NPU 606, and/or processing unit 604. The sensor 106 may also be configured on a form of a thermal imaging camera to detect a stress level, a breathing rate, a heart rate, a blood oxygen level, and other biological parameters of the user 102. The adaptive interface 206 may use machine learning algorithms and neural networks to analyze thermal imagery and detect the stress level, the breathing rate, the heart rate, the blood oxygen level, and other parameters of the user 102.

The user device 104 may communicate with the sensor 106 to obtain the time of interaction of the user 102 with the user device 104. As mentioned above, some types of sensor 106 may use the processing unit 604 in the user device 104 for applying the machine learning techniques and performing the analysis. The biological parameters, the time of the detection of biological parameters of the user by the sensor 106, and data related to the user interaction with the user device 104 may be sent by the sensor 106 and the user device 104 to the adaptive interface 206.

The adaptive interface 206 may customize the data displayed by the user interface 602 based on data received from the sensor 106 and/or the user device 104. The adaptive interface 206 may use the processing units of the user device 104, such as a CPU, a GPU, and/or the NPU 606 of the user device 104. The adaptive interface 206 may use different types of machine learning techniques, such as supervised machine learning, semi-supervised machine learning, unsupervised machine learning, federated and/or collaborative machine learning, to customize the output data of the user device 104, such as graphics and audio, for the user 102 based on the biological data received from the sensor 106 and data on the user interaction from the user device 104.

The adaptive interface 206 may send the adapted and customized output data to the user interface 602. The user interface 602 may display the adapted and customized data on a screen of the user device 104.

The user device 104 may use the displaying unit 608 to display the output data in a customized format provided by the adaptive interface 206. The cycle of customizing of the output data of the user device 104 repeats in real-time so the continuously collected user data and data on user interaction with the user device 104 are used to update the graphics and audio of the user device by the adaptive interface 206. The analysis of the user data by using machine learning of the adaptive interface 206 to adapt the output data in order to elicit the change of the biological parameters of the user 102 may result in a faster processing of the user data and customized user experience for the user 102 using the user device 140.

As improvements in per-transistor speed and energy efficiency diminish, radical departures from conventional approaches are needed to continue improvements in the performance and energy efficiency of general-purpose processors. One such departure is approximate computing, where an error in computation is acceptable and the traditional robust digital abstraction of near-perfect accuracy is relaxed. Conventional techniques in energy-efficient computing navigate a design space defined by the two dimensions—performance and energy—and traditionally trade one for the other. General-purpose approximate computing explores a third dimension—error—and trades the accuracy of computation for gains in both energy and performance. Techniques to harvest large savings from small errors have proven elusive. The present disclosure describes an approach that uses machine learning-based transformations to accelerate approximation-tolerant programs. The core idea is to train a learning model how an approximable region of a code—a code that can produce imprecise but acceptable results—behaves and replace the original code region with an efficient computation of the learned model. Neural networks are used to learn code behavior and approximate the code behavior. The Parrot algorithmic transformation may be used, which leverages a simple programmer annotation ("approximable") to transform a code region from a von Neumann model to a neural model. After the learning phase, the compiler replaces the original code with an invocation of a low-power accelerator called an NPU. The NPU is tightly coupled to the processor to permit profitable acceleration even when small regions of code are transformed. Offloading approximable code regions to the NPU is faster and more energy efficient than executing the original code. For a set of diverse applications, NPU acceleration provides whole-application speed increase up to 2.3 times and energy savings of up to 3 times on average with an average quality loss of 9.6% at most. The NPU forms a new class of accelerators and shows that significant gains in both performance and efficiency are achievable when the traditional abstraction of near-perfect accuracy is relaxed in general-purpose computing. It is widely understood that energy efficiency now fundamentally limits microprocessor performance gains.

Figure 7:
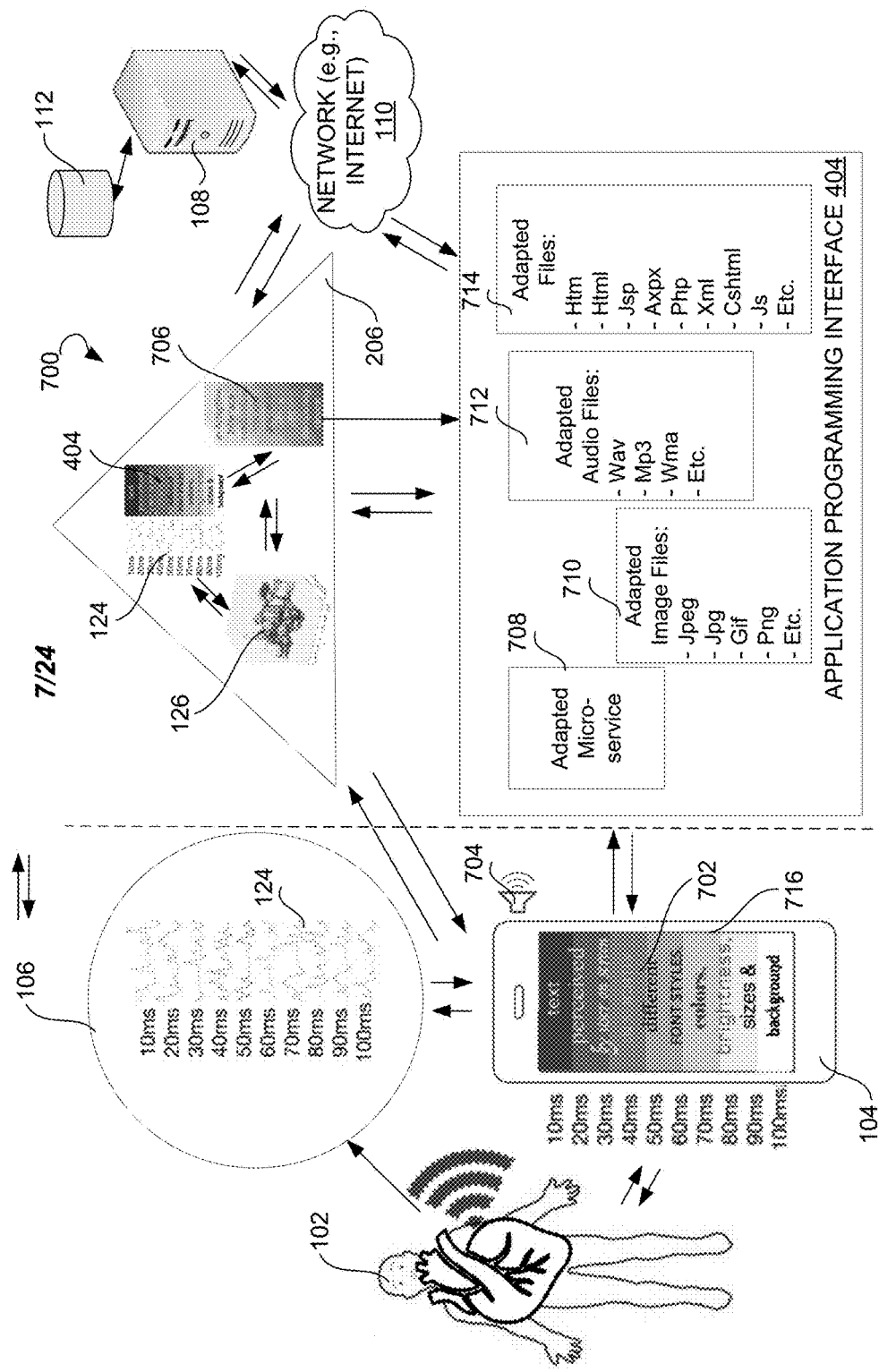
FIG. 7 is a schematic diagram that illustrates operations performed by an adaptive interface to customize output on a user device based on user data, in accordance with some example embodiments.

FIG. 7 is a schematic diagram 700 that illustrates operations performed by an adaptive interface to customize output on a user device based on user data, according to an example embodiment. The user 102 may interact with a user device 104 by reviewing graphics 702 shown on a user interface 716 of the user device 104 and listening to audio 704 produced by the user device 104. A sensor 106 may continuously sense user data 124 during the interaction of the user 102 with the user device 104.

The user device 104 may provide data related to output data currently shown to the user on the user interface 716 to the adaptive interface 206. Furthermore, the sensor 106 may provide the sensed user data 124 to the user device 104, and the user device 104 may analyze the sensed user data 124 and provide the results of the analysis to the adaptive interface 206.

The adaptive interface 206 may process the data related to output data currently shown to the user on the user interface 716 and the analyzed user data 124 using machine learning techniques 126. Based on the processing, the adaptive interface 206 may continuously customize output data of the user device 104 and provide customized output data 706 to the API 404 of the user device 104. Upon receipt of the customized output data 706, the API 404 may provide the customized output data 706 to the user 102 on a display of the user device 104.

The customized output data 706 may include one or more of the following: an adapted microservice 708, adapted image files 710 (e.g., in JPEG, JPG, GIF, PNG, and other formats), adapted audio files 712 (e.g., in WAV, MP3, WMA, and other formats), adapted files 714 (e.g., in HTM, HTML, JSP, AXPX, PHPH, XML, CSHTML, JS, and other formats), and so forth.

Figure 8:
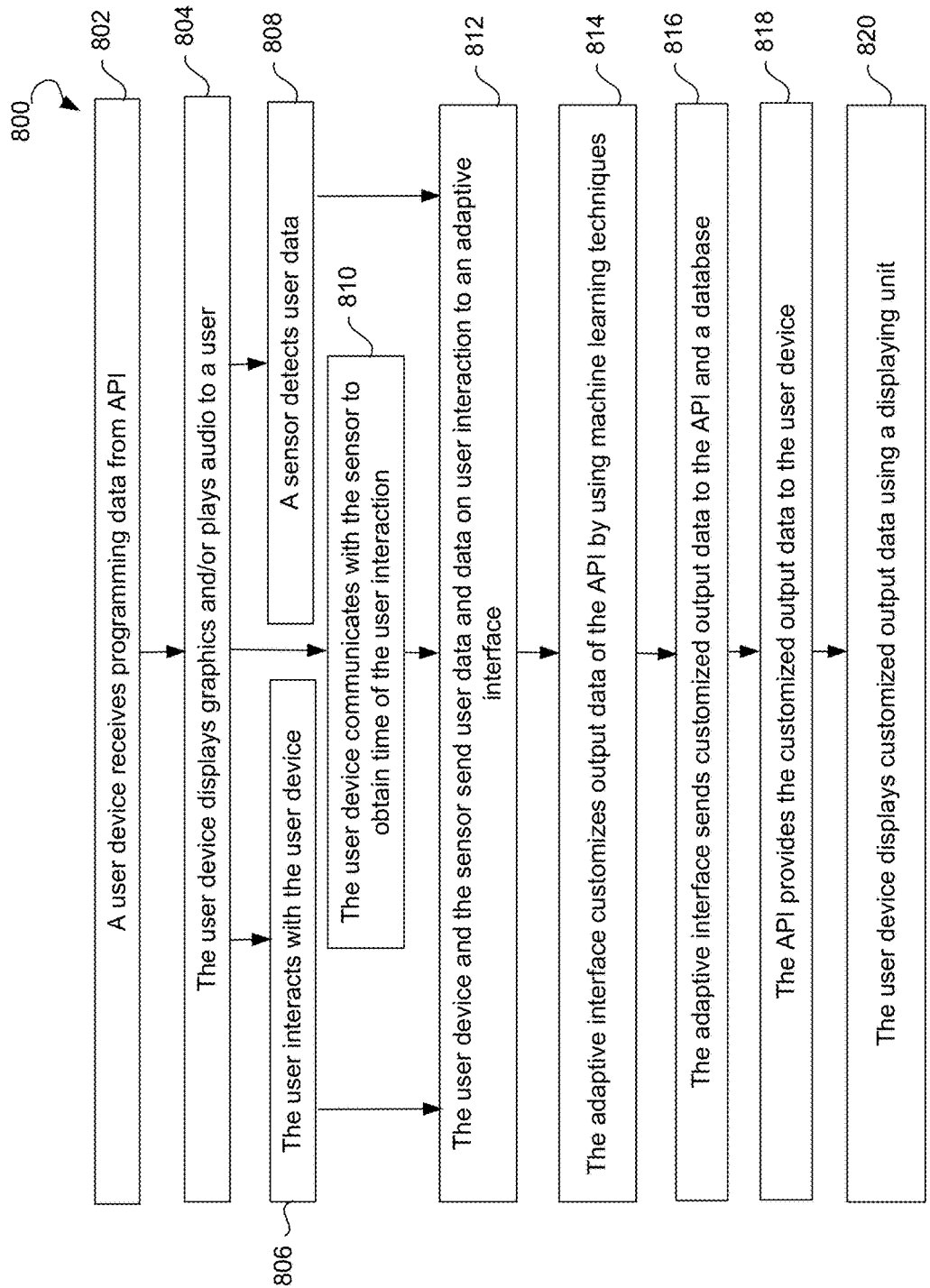
FIG. 8 is a flow chart illustrating customization of output data of a user device based on user data, in accordance with some example embodiments.

FIG. 8 is a flow chart 800 illustrating customizing output of a user device based on user data, in accordance with some example embodiments. At step 802, a user device may receive programming data from an API associated with the user device. The user device may provide the received programming data to the user at step 804 by displaying graphics on a display of the user device and playing audio using a speaker of the user device. The user may interact with the user device, e.g., by viewing the graphics displayed on the user device and listening to the audio played the user device, as shown by step 806. User data, such as biological data of the user, may be continuously sensed by a sensor as shown by step 808. Additionally, the user device may communicate with the sensor at step 810 to obtain the time of the user interaction with the user device. The time of interaction may be used for determining a dependency of the user data on the interaction of the user with the user device at each moment of time.

At step 812, the user device and the sensor may send user data and data on user interaction to an adaptive interface. The adaptive interface may customize output data of the API of the user device by using machine learning techniques at step 814. Specifically, the adaptive interface may analyze the user data and select changes to be done to the output data of the API to cause changing of the user data. For example, the adaptive interface may analyze blood pressure of the user, determine that the user pressure exceeds a predetermined value, review historical data related to dependency of the user pressure on visual and audio data provided to the user on the user device, and customize the visual and audio data to elicit decreasing of the blood pressure of the user.

The adaptive interface may send the customized output data to the API of the user device at step 816. Additionally, the adaptive interface may store the customized output data to a database as historical data. The historical data may be used in further customization of the output data. At step 818, the API may provide the customized output data to the user device. The user device may display the customized output data using a displaying unit at step 820.

Figure 9:
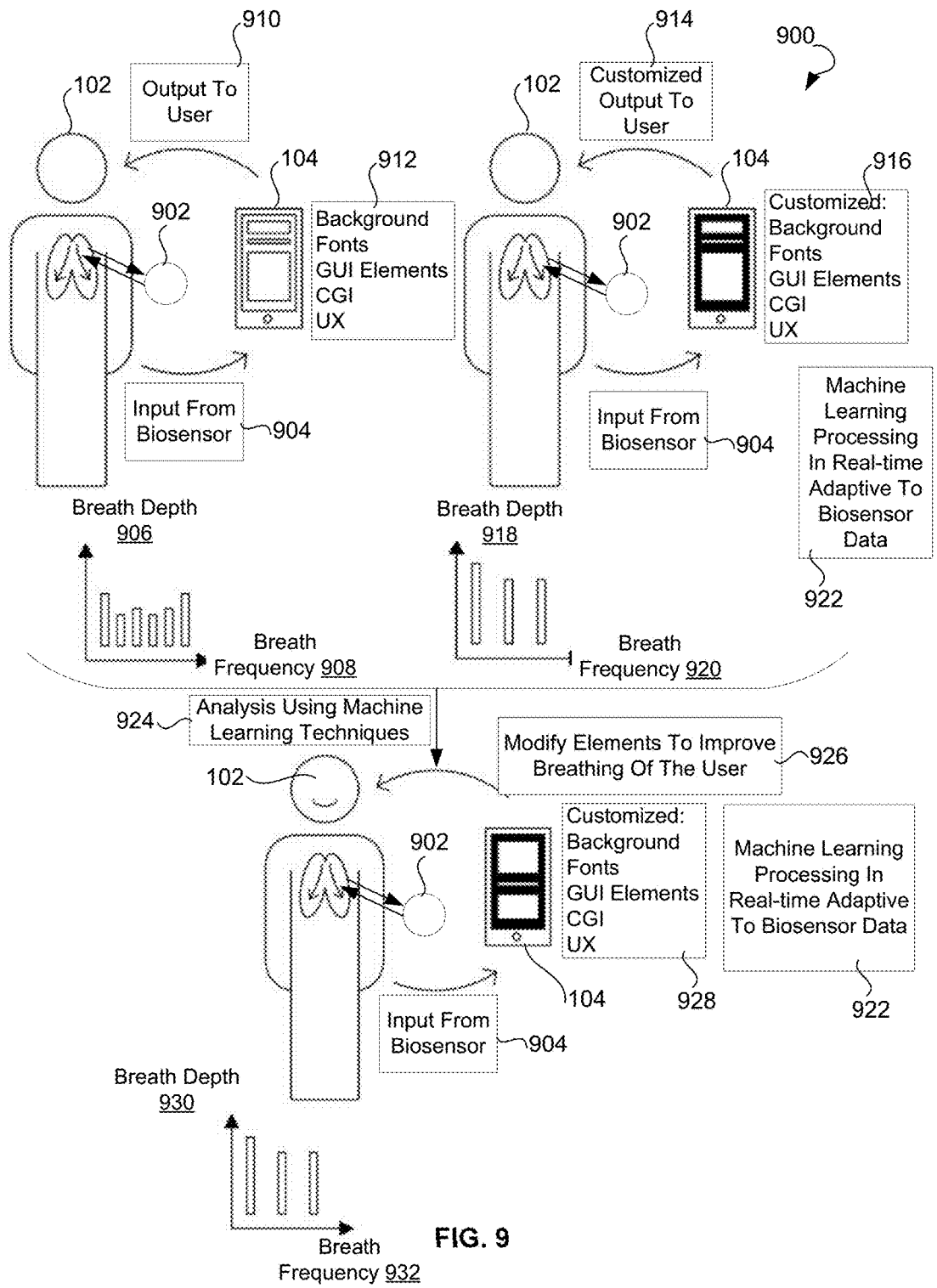
FIG. 9 is a schematic diagram showing customization of output data on a user device based on biological data of a user, according to an example embodiment.

FIG. 9 is a schematic diagram 900 showing customization of output data on a user device based on biological data of a user, according to an example embodiment. The breath of a user 102 may be continuously monitored by a biosensor 902, such as a breath sensor. User data collected by the biosensor 902 may be provided to a user device 104 as an input 904 from the biosensor 902. The user device 104 may provide the input 904 from the biosensor 902 to a computing resource. The computing resource may analyze the input 904 from the biosensor 902. In an example embodiment, the analysis may include determining breath depth 906 and breath frequency 908. The computing resource may provide the results of the analysis to an adaptive interface. Additionally, the user device 104 may also provide, to an adaptive interface, data related to output 910 viewed by the user 102 at the time the biosensor 902 collected the user data. The output 910 provided to the user 102 on the user device 104 may include graphics 912 shown to the user 102 using the user device 104, such as background, fonts, GUI elements, CGI, UX, and the like.

The adaptive interface may process the results of the analysis, the output 910 viewed by the user 102, and historical data previously collected for the user 102 and/or a plurality of users on dependency of biological data of the user 102 and/or the plurality of users on the output 910 viewed on the user device 104. The adaptive interface may perform the processing 922 using machine learning techniques. Based on the processing, the adaptive interface may customize the output 910 to provoke changing of the user data (e.g., to provoke deeper inhales of the user 102). The adaptive interface may provide customized output 914 to the user device 104. The customized output 914 provided to the user 102 on the user device 104 may include customized graphics 916 shown to the user 102 using the user device 104, such as customized background, fonts, GUI elements, CGI, UX, and the like.

The biosensor 902 may continue monitoring the user data and provide the data collected based on the monitoring to the computing resource. The computing resource may analyze the input 904 from the biosensor 902. In an example embodiment, the analysis may include determining breath depth 918 and breath frequency 920 that the user has after reviewing the customized output 914.

The user data continuously collected by the biosensor 902 and the customized output 914 provided to the user 102 may be continuously analyzed by the adaptive interface. The adaptive interface may continue applying the machine learning techniques for the analysis 924. Based on the analysis 924 and machine learning processing 922 in real-time, the elements of graphics 928 provided to the user 102 on a user interface of the user device 104 may be continuously modified, as shown by block 926, to elicit improved breathing of the user 102. The breath depth 930 and breath frequency 932 of the user 102 may be continuously analyzed by the adaptive interface for further modification of the output of the user device 102.

Figure 10:
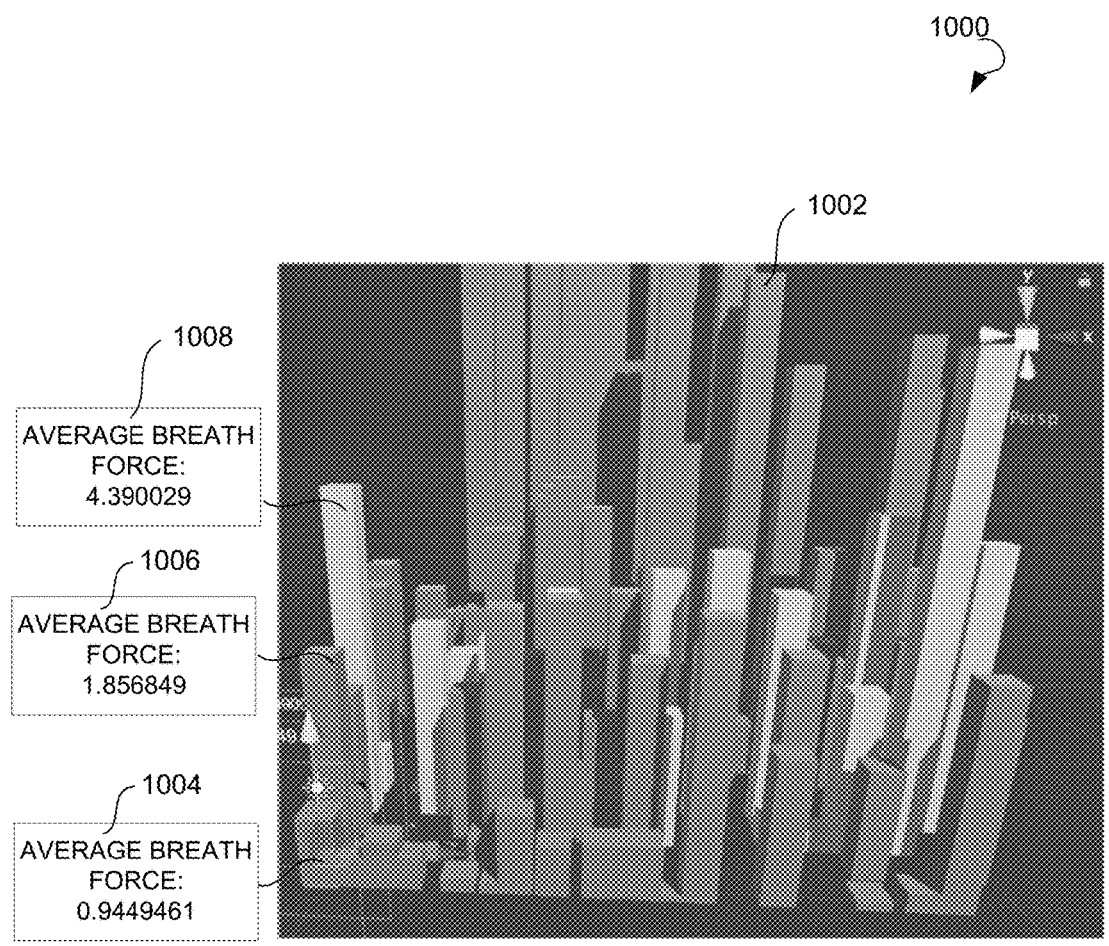
FIG. 10 is a schematic diagram illustrating processing data from a sensor using machine learning processing, according to an example embodiment.

FIG. 10 is a schematic diagram 1000 illustrating processing data from a sensor using machine learning techniques, according to an example embodiment. The sensor, such as a breath sensor, may provide detected data as an input to an adaptive interface. The adaptive interface may process the input from the sensor in a machine learning environment using machine learning algorithms. The adaptive interface may continuously learn about user response to providing customized visual and audio output data to the user using the user device. The user response may include changing of the biological parameters of the user invoked by reviewing the customized visual and audio output data by the user. The biological parameters may include an average breath force 1004 sensed by the sensor and an average breath force 1006 and 1008 further sensed by the sensor upon providing the customized visual and audio output data to the user.

Figure 11:
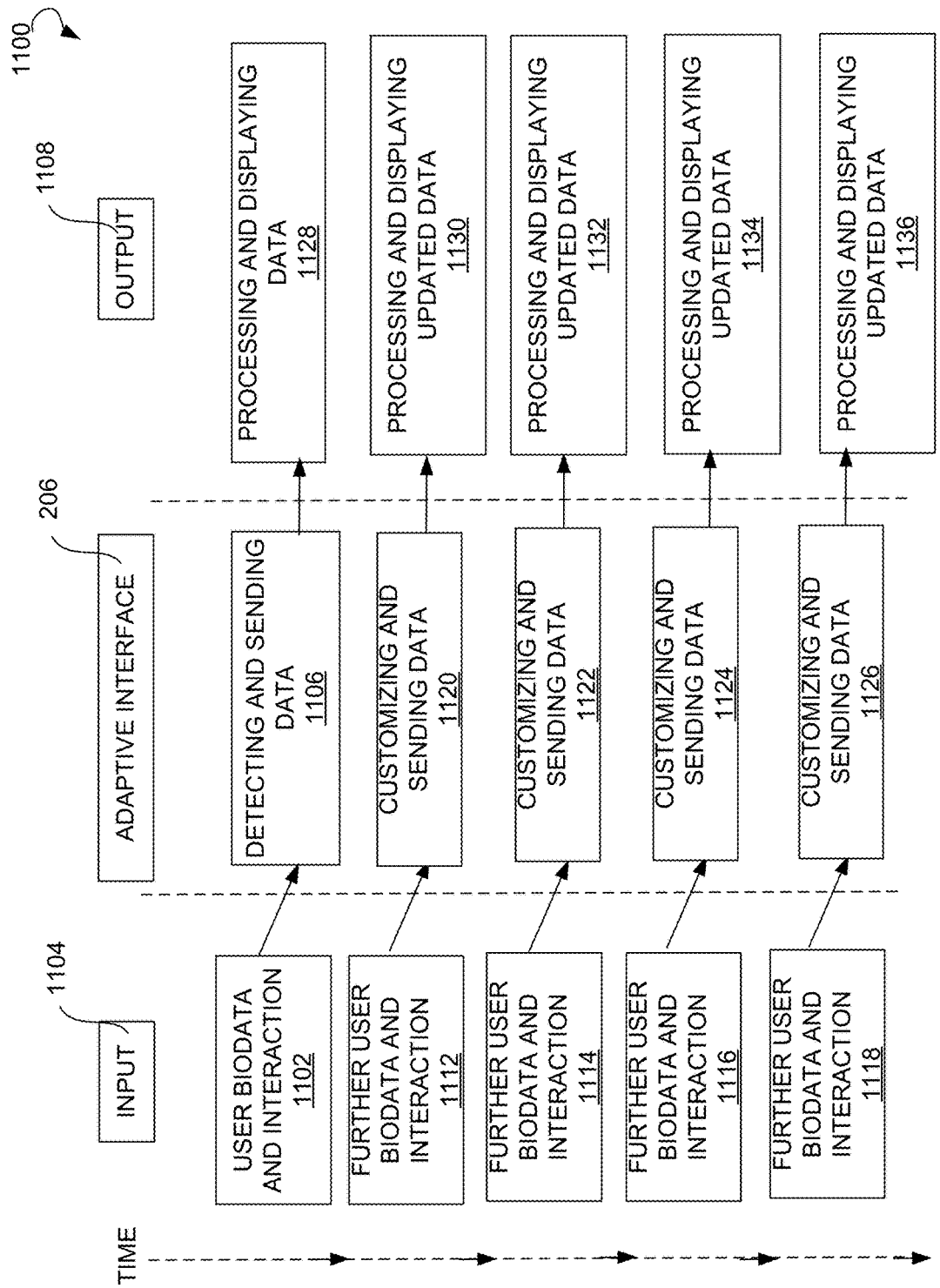
FIG. 11 is a flow chart illustrating continuous customization of output based on user data, according to an example embodiment.

FIG. 11 is a flow chart 1100 illustrating continuous customization of output based on user data, according to an example embodiment. Data related to biological parameters of the user and interaction of the user with a user device may be continuously captured by a sensor and the user device in a form of user biodata and interaction 1102. The captured biological data, also referred to as biodata, and data on interaction 1102 may be provided to an adaptive interface 206 as input 1104. At step 1106, the adaptive interface 206 may detect the user biodata and interaction 1102 and send the data to be displayed by a user device as output 1108. A displaying unit of the user device may process the data received from the adaptive interface 206 and provide the output on the user device, as shown by block 1110. The output may be provided by displaying visual data, playing audio data, providing haptic feedback, and so forth.

The sensor and the user device may continuously provide further user biodata and data on interaction, as shown by blocks 1112, 1114, 1116, and 1118. The adaptive interface 206 may apply the machine learning techniques to customize the output of the user device and send the customized output to the user device, as shown by blocks 1120, 1122, 1124, and 1126. The displaying unit of the user device may process the customized data received from the adaptive interface 206 and provide the updated data on the user device, as shown by blocks 1128, 1130, 1132, 1134, and 1136.

Figure 12:
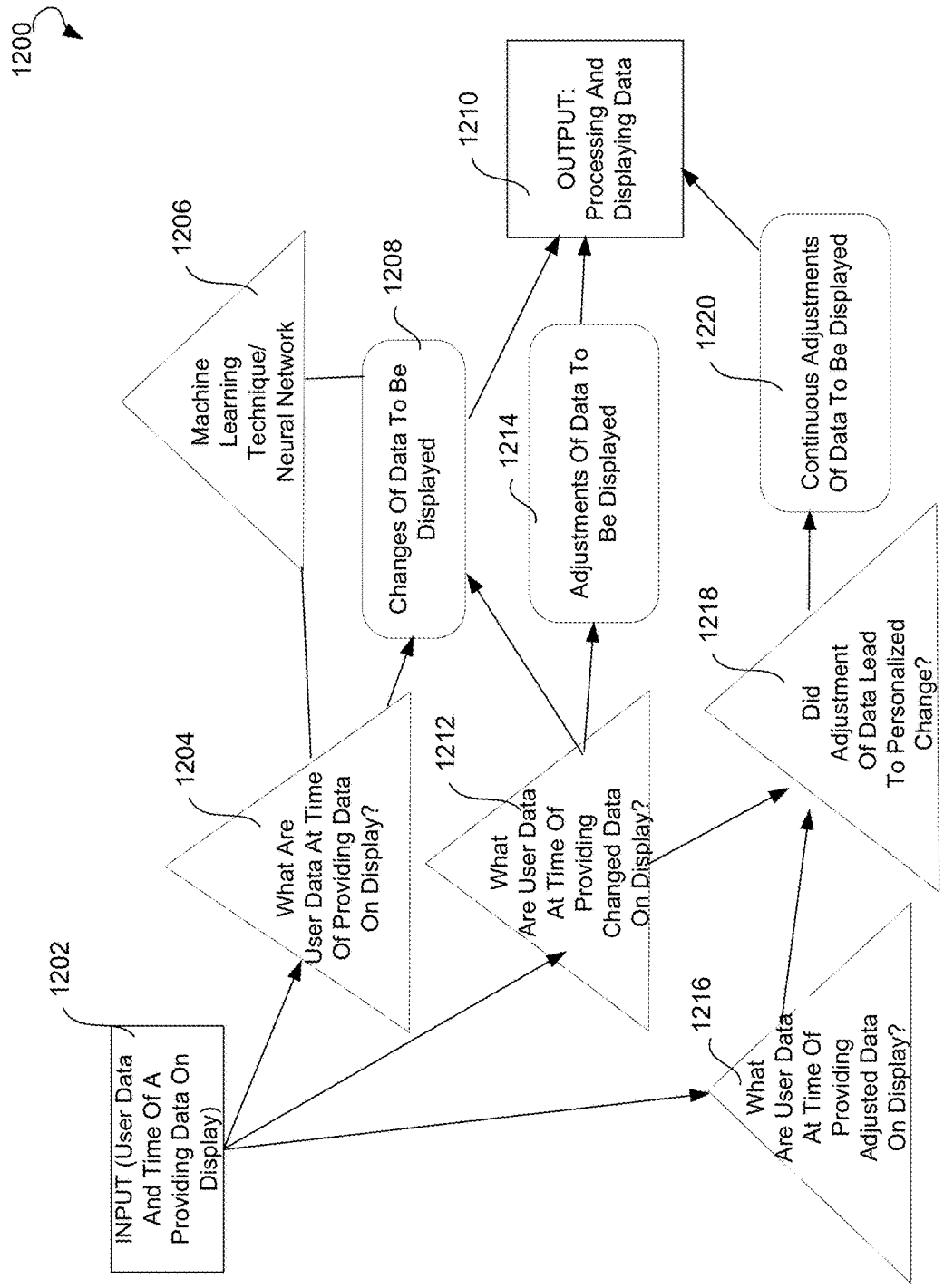
FIG. 12 is a schematic diagram showing operations performed by an adaptive interface to continuously customize output data using machine learning techniques, according to an example embodiment.

FIG. 12 is a schematic diagram 1200 showing operations performed by an adaptive interface to continuously customize output data using machine learning techniques, according to an example embodiment. The adaptive interface may continuously receive input 1202 from a user device. The input 1202 may include user data sensed by a sensor and time of providing data, e.g., graphics, on a display of the user device to the user. At block 1204, based on the input 1202, the adaptive interface may determine which user data the user had at a time of providing the data on the display. For example, the adaptive interface may determine the blood pressure the user had when the user read information on a green font of a webpage displayed on the user device. The adaptive interface may apply machine learning techniques and neural networks 1206 to determine whether the user data need to be changed according to predetermined criteria (e.g., whether the blood pressure of the user is above a predetermined value at the current moment of time). The adaptive interface may further apply machine learning techniques and neural networks 1206 to determine specific changes 1208 to be applied to the output data of the user device to cause changing of the user data (e.g., to cause decreasing of the blood pressure of the user). The adaptive interface may send the changed data to be displayed to the user device. A displaying unit of the user device may process and display the changed data as the output 1210 of the user device.

The adaptive interface may continue receiving input 1202 from the user device. Specifically, the adaptive interface may receive user data sensed by the sensor and time of providing changed data on the display of the user device to the user. Based on the input 1202, the adaptive interface may determine which user data the user had at a time of providing the changed data on the display, as shown by block 1212. The adaptive interface may determine whether the user data still needs to be changed (e.g., if the blood pressure of the user is still above the predetermined value). If the user data still needs to be changed, the adaptive interface may determine, at block 1214, which adjustments of data to be displayed to the user need to be made. The adaptive interface may send the adjusted data to be displayed to the user device. The displaying unit of the user device may process and display the adjusted data as the output 1210 of the user device.

Upon providing the adjusted data, the adaptive interface may continue receiving input 1202 from the user device. Specifically, the adaptive interface may receive user data sensed by the sensor and time of providing the adjusted data on the display of the user device to the user. Based on the input 1202, the adaptive interface may determine which user data the user had at a time of providing the adjusted data on the display, as shown by block 1216. At block 1218, the adaptive interface may determine whether the adjustment of data to be displayed to the user led to a personalized change (i.e. to the change of biological parameters of the user). The adaptive interface may perform continuous adjustment of data to be displayed to the user, as shown by block 1220. The adaptive interface may continuously provide the adjusted data as the output 1210 to the user device.

Figure 13:
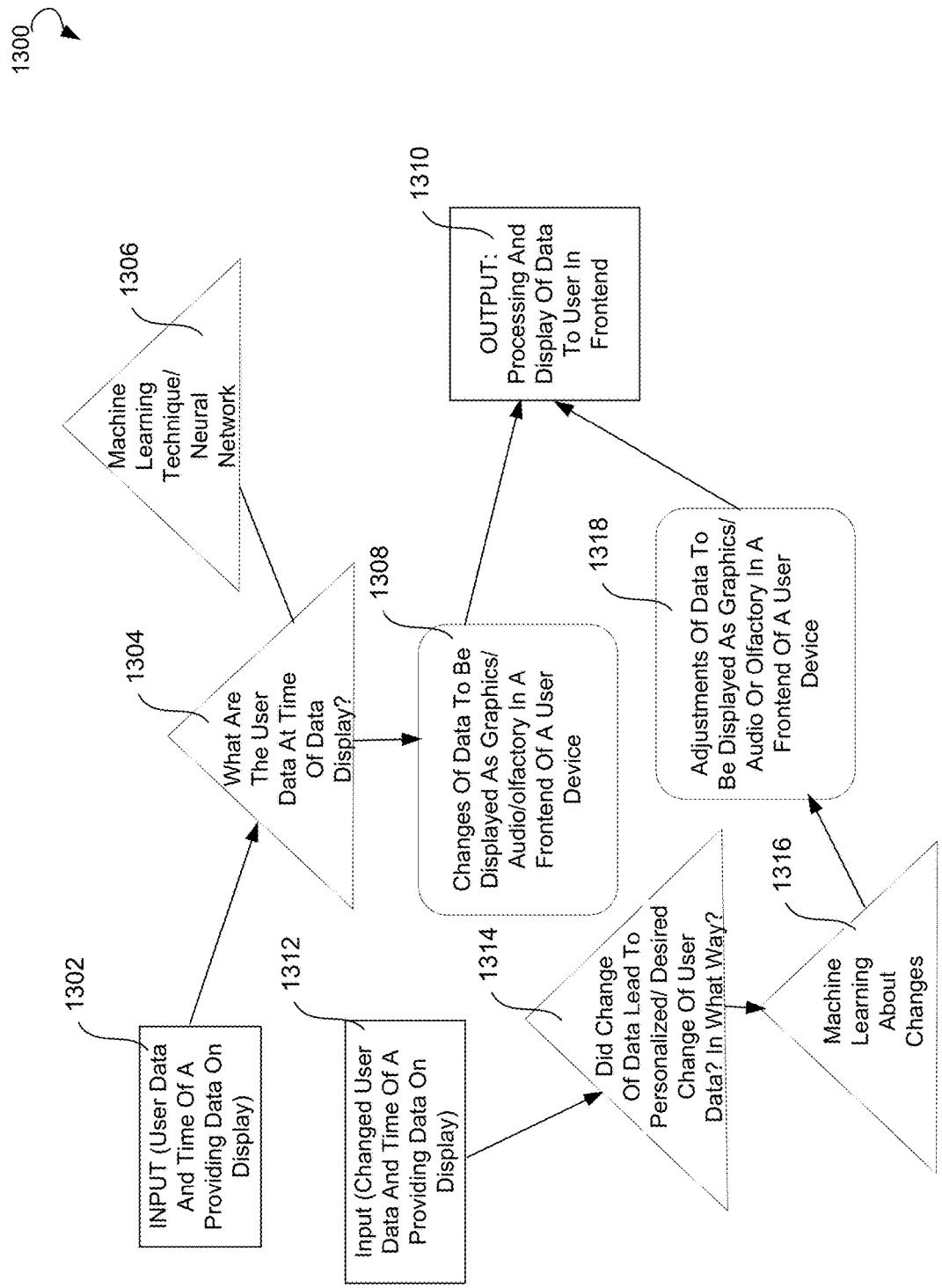
FIG. 13 is a schematic diagram showing operations performed by an adaptive interface to continuously customize output data using machine learning techniques, according to an example embodiment.

FIG. 13 is a schematic diagram 1300 showing operations performed by an adaptive interface to continuously customize output data using machine learning techniques, according to an example embodiment. The adaptive interface may continuously receive input 1302 from a user device. The input 1302 may include user data sensed by a sensor and time of providing data, e.g., output data in a form of graphics, on a display of the user device to the user. Based on the input 1302, the adaptive interface may determine which user data the user had at a time of providing the data on the display at block 1304. The adaptive interface may apply machine learning techniques and neural networks 1306 to determine whether the user data needs to be changed according to predetermined criteria. The adaptive interface may further apply machine learning techniques and neural networks 1306 to determine specific changes 1308 to be applied to the output data, e.g., graphics, audio, or olfactory data, of the user device to cause changing of the user data. The adaptive interface may send the changed data to be displayed in a frontend, i.e., on a display of the user device. A displaying unit of the user device may process and display the changed data as the output 1310 of the user device.

The adaptive interface may receive further input 1312 from the user device. The input 1312 may include changed user data sensed by the sensor and time of providing changed data on the display of the user device to the user. Based on the input 1312, the adaptive interface may determine whether the change of the output data led to personalized or desired change of the user data, as shown by block 1314. Specifically, the adaptive interface may determine in which way the user data changed in response to providing the changed output data to the user. The adaptive interface may further apply machine learning techniques and neural networks 1316 to determine adjustments 1318 to be applied to the changed output data of the user device to cause further changing of the user data. The adaptive interface may send the adjusted data to be displayed in the frontend (i.e., on the display of the user device). The displaying unit of the user device may process and display the adjusted data as the output 1310 of the user device.

Figure 14:
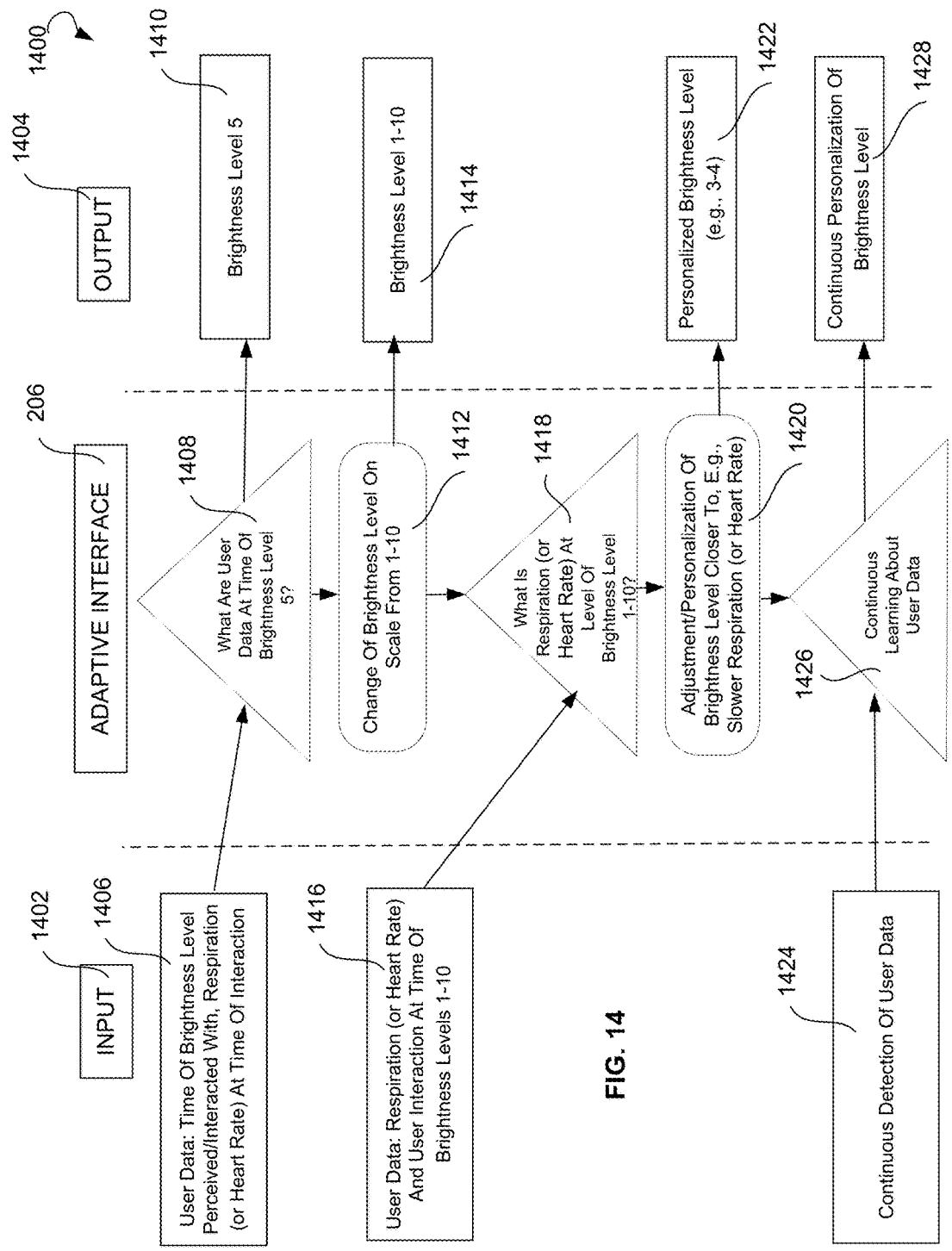
FIG. 14 is a block diagram illustrating continuous personalization of a brightness level on a user device based on data related to respiration or heart rate of a user, according to an example embodiment.

FIG. 14 is a block diagram 1400 illustrating continuous personalization of a brightness level on a user device based on data related to respiration or heart rate of a user, according to an example embodiment. The respiration may be determined based on respiratory muscle movements, thermal changes of skin, movement of belly or chest, a heart rate, and so forth. An input 1402 may be continuously provided to an adaptive interface 206. The adaptive interface 206 may process the input 1402 and provide an output 1404 for displaying on the user device.

Specifically, user data 1406 may be provided as the input 1402 to the adaptive interface 206. The user data 1406 may include data related to respiration or a heart rate of the user at the time of interaction of the user with the user device having a particular brightness level. The user data 1406 may further include a time when the user interacted with or perceived the particular brightness level of the user device. The adaptive interface 206 may determine, at block 1408, which user data the user had at a particular time when the user device had a particular brightness level (e.g., what respiration and heart rate the user had at the time when the brightness level of the user device was 5) as shown by block 1410.

At block 1412, the adaptive interface 206 may change the brightness level on a scale from 1 to 10 to cause the change of the respiration of the heart rate of the user. The determination whether the brightness level needs to be changed and to what value may be made using machine learning techniques based on historical data of the user or a plurality of users. Upon setting the brightness level 1414 of the user device from 1 to 10, the adaptive interface 206 may receive further user input data 1416. The further user data 1416 may include data related to respiration or the heart rate of the user at the time of interaction of the user with the user device having the brightness level 1414 from 1 to 10. The user data 1406 may further include a time when the user interacted with or perceived the brightness level 1414 from 1 to 10 of the user device.

The adaptive interface 206 may determine, at block 1418, which user data the user had at particular time when the user device had the brightness level 1414 (e.g., what respiration and heart rate the user had at the time when the brightness level 1414 of the user device was from 1 to 10). At block 1420, the adaptive interface 206 may select an adjusted, i.e., personalized, value of brightness level intended, for example, to slow the respiration or the heart rate of the user. The personalized brightness level 1422 (e.g., 3-4) selected by the adaptive interface 206 may be set on the user device.

Upon setting the personalized brightness level 1422 of the user device, the adaptive interface 206 may receive continuously detected user data 1424. At block 1426, the adaptive interface 206 may determine which user data the user had at a particular time when the user device had the personalized brightness level 1422. The adaptive interface 206 may perform continuous personalization of the brightness level at block 1428 to elicit a personalized change of user data, such as the respiration or the heart rate of the user.

Figure 15:
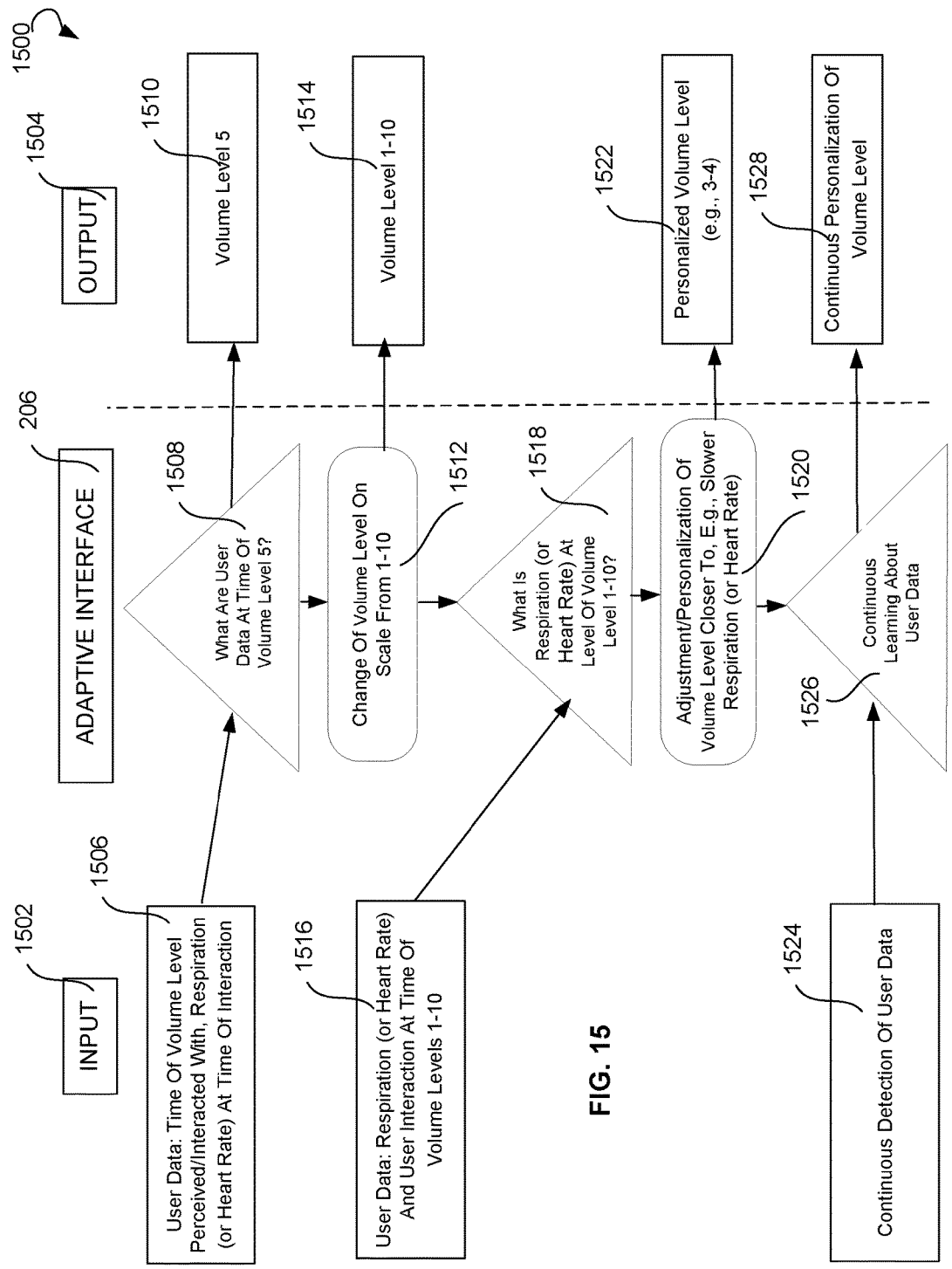
FIG. 15 is a block diagram illustrating continuous personalization of a volume level on a user device based on data related to respiration or heart rate of a user, according to an example embodiment.

FIG. 15 is a block diagram 1500 illustrating continuous personalization of a volume level on a user device based on data related to respiration or a heart rate of a user, according to an example embodiment. An input 1502 may be continuously provided to an adaptive interface 206. The adaptive interface 206 may process the input 1502 and provide an output 1504 for displaying on the user device.

Specifically, user data 1506 may be provided to the adaptive interface 206. The user data 1506 may include data related to respiration or the heart rate of the user at the time of interaction of the user with the user device having a particular volume level. The user data 1506 may further include a time when the user interacted with or perceived the particular volume level of the user device. The adaptive interface 206 may determine, at block 1508, which user data the user had at a particular time when the user device had a particular volume level (e.g., what respiration and heart rate the user had at the time when the volume level of the user device was 5), as shown by block 1510.

At block 1512, the adaptive interface 206 may change the volume level on a scale from 1 to 10 to cause the change of the respiration of heart rate of the user. The determination whether the volume level needs to be changed and to what value may be made using machine learning techniques based on historical data of the user or a plurality of users. Upon setting the volume level 1514 of the user device from 1 to 10, the adaptive interface 206 may receive further user input data 1516. The further user data 1516 may include data related to respiration or the heart rate of the user at the time of interaction of the user with the user device having the volume level 1514 from 1 to 10. The user data 1506 may further include time when the user interacted with or perceived the volume level 1514 from 1 to 10 of the user device.

The adaptive interface 206 may determine, at block 1518, which user data the user had at a particular time when the user device had the volume level 1514 (e.g., what respiration and heart rate the user had at the time when the volume level 1514 of the user device was from 1 to 10). At block 1520, the adaptive interface 206 may select an adjusted value of the volume level intended, for example, to slower the respiration or the heart rate of the user. The personalized volume level 1522 (e.g., 3-4) selected by the adaptive interface 206 may be set on the user device.

Upon setting the personalized volume level 1522 of the user device, the adaptive interface 206 may receive continuously detected user data 1524. At block 1526, the adaptive interface 206 may determine which user data the user had at particular time when the user device had the personalized volume level 1522. The adaptive interface 206 may perform continuous personalization of the volume level at block 1528 to elicit a personalized change of user data, such as the respiration or the heart rate of the user.

Figure 16:
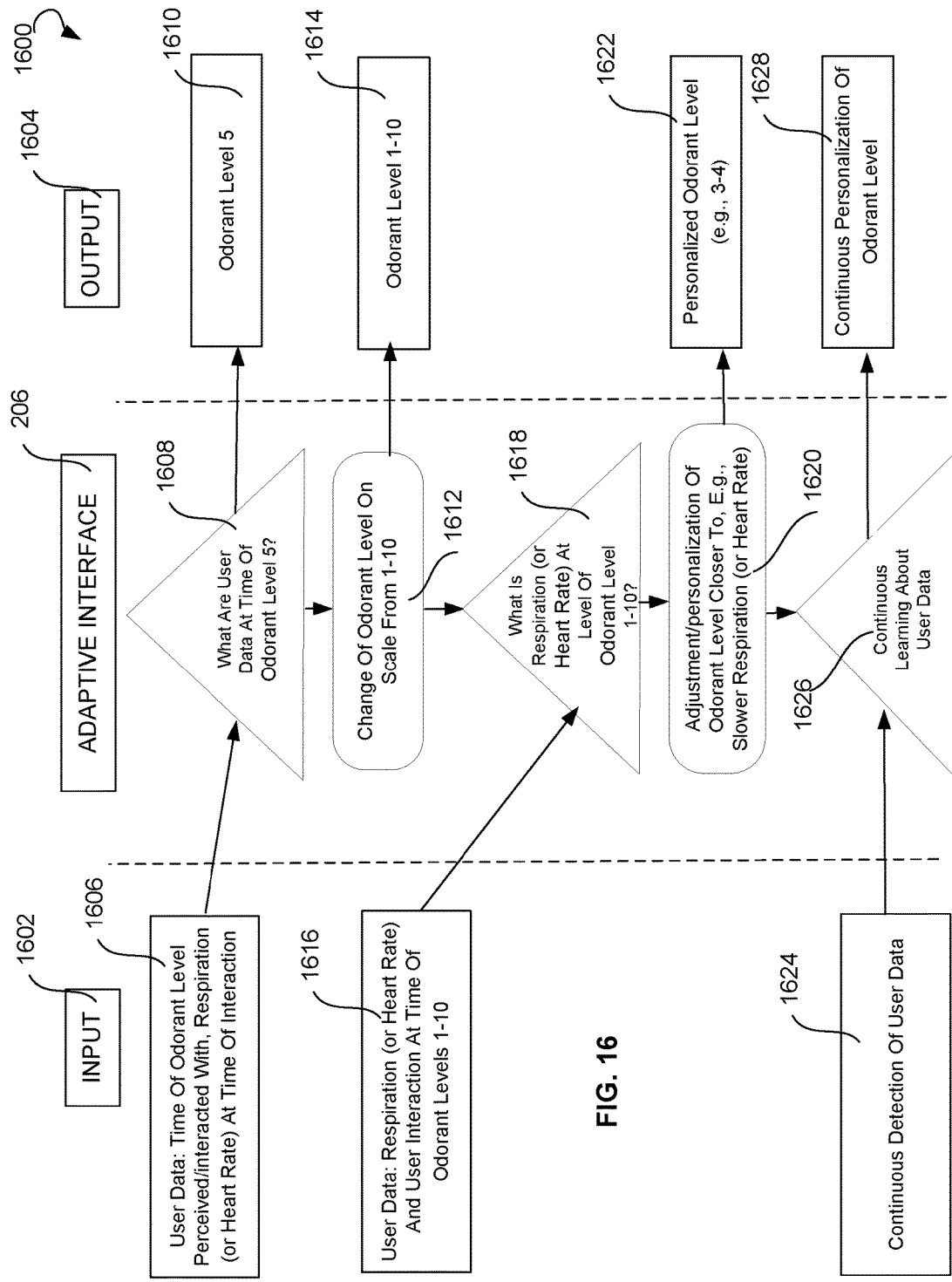
FIG. 16 is a block diagram illustrating continuous personalization of an odorant level on a user device based on data related to respiration or heart rate of a user, according to an example embodiment.

FIG. 16 is a block diagram 1600 illustrating continuous personalization of an odorant level on a user device based on data related to respiration or a heart rate of a user, according to an example embodiment. An input 1602 may be continuously provided to an adaptive interface 206. The adaptive interface 206 may process the input 1602 and provide an output 1604 for displaying on the user device. The user device may include an artificial olfaction device 122 as shown on FIG. 1.

User data 1606 may be provided to the adaptive interface 206. The user data 1606 may include data related to respiration or the heart rate of the user at the time of interaction of the user with the user device having a particular volume level. The user data 1606 may further include a time when the user interacted with or perceived the particular odorant level of the user device. The adaptive interface 206 may determine, at block 1608, which user data the user had at a particular time when the user device had a particular odorant level (e.g., what respiration and heart rate the user had at the time when the odorant level of the user device was 5), as shown by block 1610.

At block 1612, the adaptive interface 206 may change the odorant level on a scale from 1 to 10 to cause the change of the respiration of heart rate of the user. The determination whether the odorant level needs to be changed and to what value may be made using machine learning techniques based on historical data of the user or a plurality of users. Upon setting the odorant level 1614 of the user device from 1 to 10, the adaptive interface 206 may receive further user input data 1616. The further user data 1616 may include data related to respiration or the heart rate of the user at the time of interaction of the user with the user device having the odorant level 1614 from 1 to 10. The user data 1616 may further include a time when the user interacted with or perceived the odorant level 1614 from 1 to 10 of the user device.

The adaptive interface 206 may determine, at block 1618, which user data the user had at a particular time when the user device had the odorant level 1614 (e.g., what respiration and heart rate the user had at the time when the odorant level 1614 of the user device was from 1 to 10). At block 1620, the adaptive interface 206 may select a personalized value of the odorant level intended, for example, to slow the respiration or the heart rate of the user. The personalized odorant level 1622 (e.g., 3-4) selected by the adaptive interface 206 may be set on the user device.

Upon setting the personalized odorant level 1622 of the user device, the adaptive interface 206 may receive continuously detected user data 1624. At block 1626, the adaptive interface 206 may determine which user data the user had at a particular time when the user device had the personalized odorant level 1622. The adaptive interface 206 may perform continuous personalization of the odorant level at block 1628 to elicit a personalized change of user data, such as the respiration or the heart rate of the user.

Figure 17:
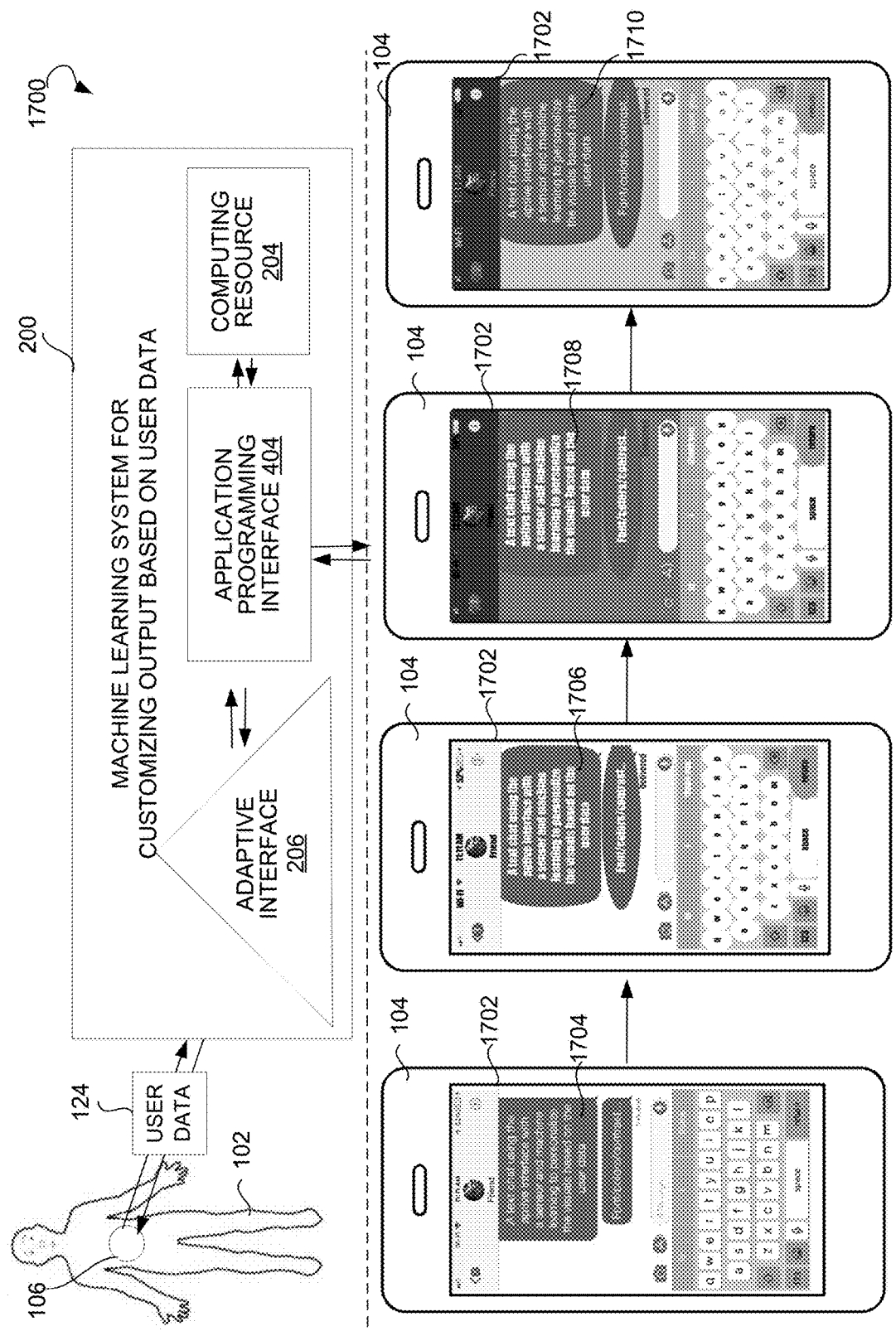
FIG. 17 is a schematic diagram showing a user interface of a mobile device customized by a machine learning system for customizing output based on user data, according to an example embodiment.

FIG. 17 is a schematic diagram 1700 showing a user interface of a mobile device customized by a machine learning system for customizing output based on user data, according to an example embodiment. Specifically, FIG. 17 illustrates customizing a graphics output on a user device 104 based on user data 124 sensed by a sensor 106. A user interface 1702 may display output data 1704 on a screen of the user device 104. The adaptive interface 206 of the machine learning system 200 for customizing output based on user data may customize the output data 1704 and send customized output data 1706 to the user interface 1702. The user interface 1702 may display the customized data 1706 on the screen of the user device 104. The customized output data 1706 may include a changed font, changed colors, changed brightness, changed contrast, and the like.

Upon further customization of the output data, the adaptive interface 206 may send further customized output data 1708 to the user interface 1702. The user interface 1702 may display the further customized data 1708 on the screen of the user device 104. The customized output data 1708 may include a changed font, changed colors, changed brightness, a changed contrast, a changed background, and the like.

The adaptive interface 206 may continuously customize the output data and provide the further customized output data 1710 to the user interface 1702. The user interface 1702 may display the further customized data 1710 on the screen of the user device 104.

Figure 18:
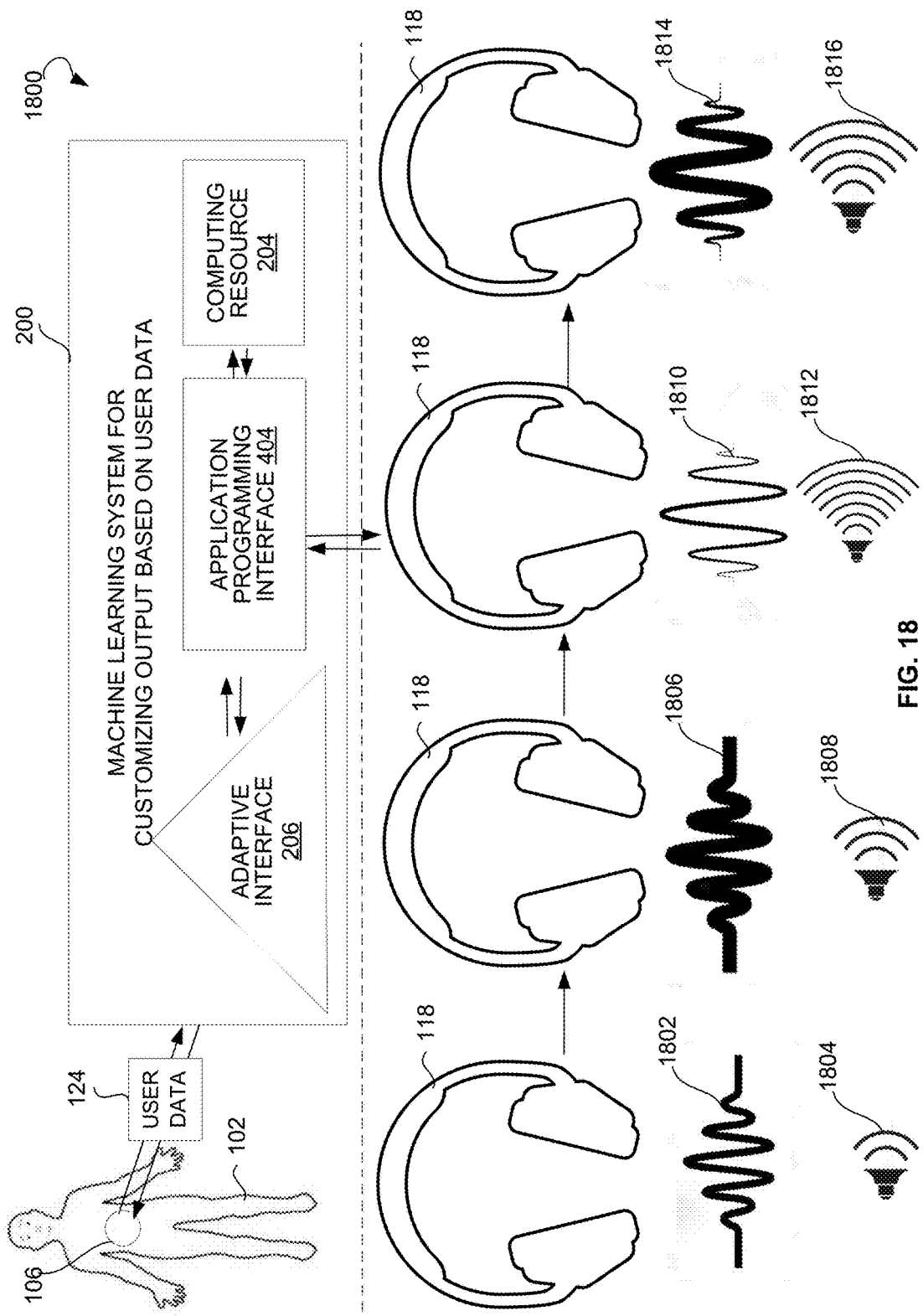
FIG. 18 is a schematic diagram showing output data of headphones customized by a machine learning system for customizing output based on user data, according to an example embodiment.

FIG. 18 is a schematic diagram 1800 showing output data of a user device customized by a machine learning system for customizing output based on user data, according to an example embodiment. Specifically, FIG. 18 illustrates customizing an audio output on headphones 118 based on user data 124 of a user 102 sensed by a sensor 106. The output data, such as a pitch 1802 and a volume 1804 of the sound, may be provided to the headphones 118. The adaptive interface 206 of the machine learning system 200 for customizing output based on user data may customize the pitch 1802 and the volume 1804 and send data associated with customized pitch 1806 and customized volume 1808 to the headphones 118. The headphones 118 may reproduce the audio output with the customized pitch 1806 and customized volume 1808.

Upon further customization of the audio output based on the user data 124, the adaptive interface 206 may send further customized pitch 1810 and further customized volume 1812 to the headphones 118. The headphones 118 may reproduce the audio output with the further customized pitch 1810 and further customized volume 1812.

The adaptive interface 206 may continuously customize the audio output and provide the further customized pitch 1814 and further customized volume 1816 to the headphones 118. The headphones 118 may reproduce the further customized pitch 1814 and further customized volume 1816 to the user 102.

Figure 19:
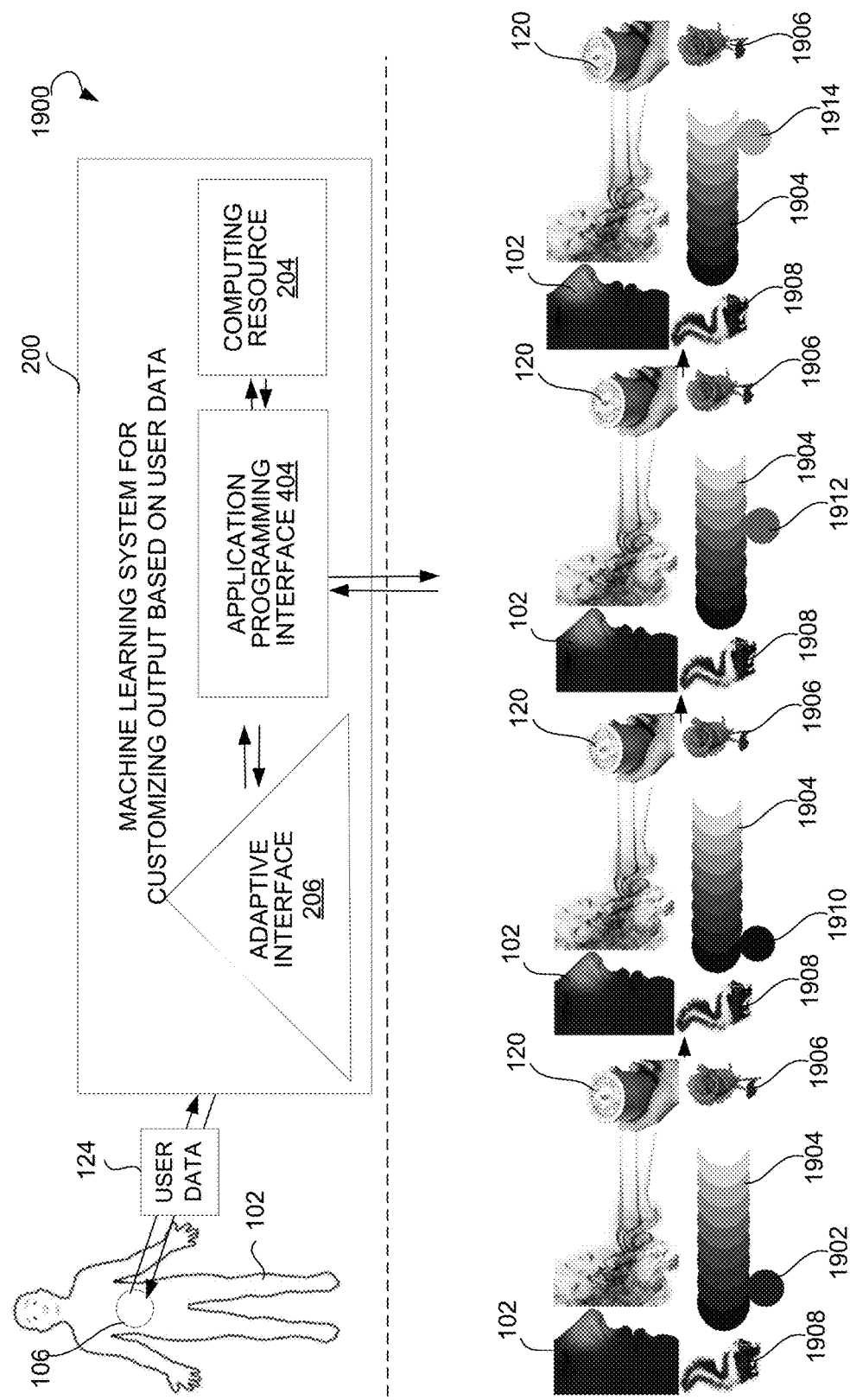
FIG. 19 is a schematic diagram showing output data of an artificial olfactory device customized by a machine learning system for customizing output based on user data, according to an example embodiment.

FIG. 19 is a schematic diagram 1900 showing output data of a user device customized by a machine learning system for customizing output based on user data, according to an example embodiment. Specifically, FIG. 19 illustrates customizing olfactory data on an artificial olfaction device 120 based on user data 124 of a user 102 sensed by a sensor 106. The output data, such as units 1902 of a perceptual axis 1904 of odorant pleasantness that ranges from very pleasant (e.g., rose as shown by element 1906) to very unpleasant (e.g., skunk as shown by element 1908), may be provided to the user 102 by the artificial olfaction device 120. The adaptive interface 206 of the machine learning system 200 for customizing output based on user data may customize the units 1902 of the perceptual axis 1904 and send customized units 1910 to the artificial olfaction device 120. The artificial olfaction device 120 may set the olfactory data according to the customized units 1910.

Upon further customization of the olfactory data based on the user data 124, the adaptive interface 206 may send further customized units 1912 of the perceptual axis 1904 to the artificial olfaction device 120. The artificial olfaction device 120 may set the olfactory data according to the customized units 1912.

The adaptive interface 206 may continuously customize the olfactory data and provide the further customized units 1914 of the perceptual axis 1904 to the artificial olfaction device 120. The artificial olfaction device 120 may set the olfactory data according to the customized units 1914.

Figure 20:
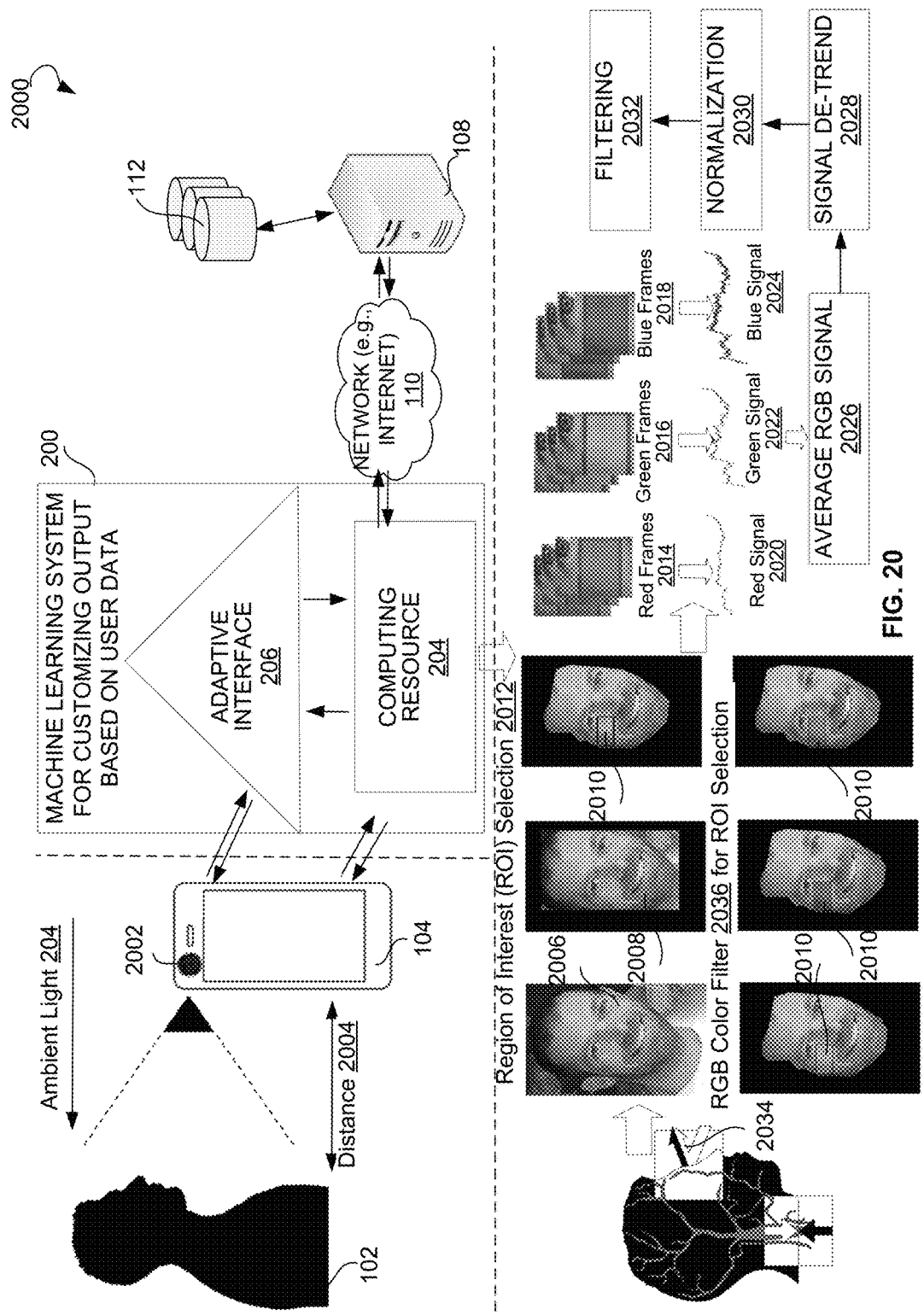
FIG. 20 is a schematic diagram showing customizing output of a user device based on user data captured by a digital camera of the user device, according to an example embodiment.

FIG. 20 is a schematic diagram 2000 showing customizing output of a user device based on user data captured by a digital camera of the user device, according to an example embodiment. The user device may include a smartphone. The digital camera shown as camera 2002 may be disposed at a distance 2004 from the user 102. The distance 2004 at which the camera 2002 may be configured to capture user data may be up to several meters or any other distance depending on parameters of the camera 2002 and environmental conditions.

In an example embodiment, the camera 2002 may be selected from a charge-coupled device, a complementary metal-oxide semiconductor image sensor, or any other type of an image sensor. The camera 2002 of the user device may be used as a non-contact and non-invasive device to measure user data. The user data may include a respiratory rate, pulse rate, blood volume pulse, and so forth. The camera 2002 may be used to capture an image the user 102. The user data captured by the camera 2002 may be processed by the adaptive interface 206 of the system 200. The processing may be performed using CPU, GPU, and/or NPU. The user data captured by the camera 2002 may be the input for the adaptive interface 206 and may be processed together with the data concerning the time of the visuals displayed to the user and audio provided to the user at the time of capture of the user data, and together with the data concerning the time of the recording of the user data.

In an example embodiment, the respiratory rate, the heart rate, and the blood volume pulse may be sensed simultaneously using the camera 2002. Specifically, the camera 2002 may capture an image 2006 of the user. Upon capturing, a part of a skin 2008 of the user 202 may be detected on the image 2006. Upon detecting the image of the skin, a region of interest 2010 may be selected as shown by step 2012. After the selection of the region of interest 2012, the changes in the average image brightness of the region of interest 2012 for a short time can be measured. The selection of the region of interest 2012 of the face may be used to obtain blood circulation features and obtain the raw blood volume pulse signal. The selection of a region of interest may influence the following heart rate detection steps. First, the selection of a region of interest may affect the tracking directly since a commonly applied tracking method uses a first frame of the captured region of interest. Second, the selected regions of interest are regarded as the source of cardiac information. The pixel values inside the region of interest can be used for intensity-based methods, while feature point locations inside the region of interest can be used for motion-based methods.

The time-lapse image of a part of the skin of the user 102 may be consecutively captured, and the changes in the average brightness of the region of interest 2010 can be measured for a period of time, for example, for 30 seconds. The brightness data can be processed by a series of operations of interpolation using a first-order derivative, a low pass filter of 2 Hz, and a sixth-order auto-regressive spectral analysis.

Remote photoplethysmography may be used for contactless monitoring of the blood volume pulse using the camera. Blood absorbs light more than the surrounding tissues and variations in blood volume affect light transmission and reflectance as schematically shown by an arrow 2034. This leads to the subtle color changes in human skin, which are invisible to human eyes but can be recorded by the camera. Various optical models can be applied to extract the intensity of color changes caused by pulse.

It is possible to capture heart rate signals at a frame rate of eight frames per second (fps), under the hypothesis that the human heartbeat frequency lies between 0.4 and 4 Hz. A frame rate between 15 and 30 fps is sufficient for heart rate detection. The estimation of the heart rate is performed by directly applying noise reduction algorithms and optical modeling methods. Alternatively, the usage of manifold learning methods mapping multidimensional face video data into one-dimensional space can be used to reveal the heart rate signal. Hemoglobin and oxyhemoglobin both have the ability of absorption in the green color range and low in the red color range. However, all three color channels (red, green, and blue) contain photoplethysmogram (PPG) information. Red green blue (RGB) color filter 2036 can be used to extract red frames 2014, green frames 2016, and blue frames 2018 from the captured image of interest 2010. Red signal 2020, green signal 2022, and blue signal 2024 can be determined based on the captured red frames 2014, green frames 2016, and blue frames 2018.

Figure 21:
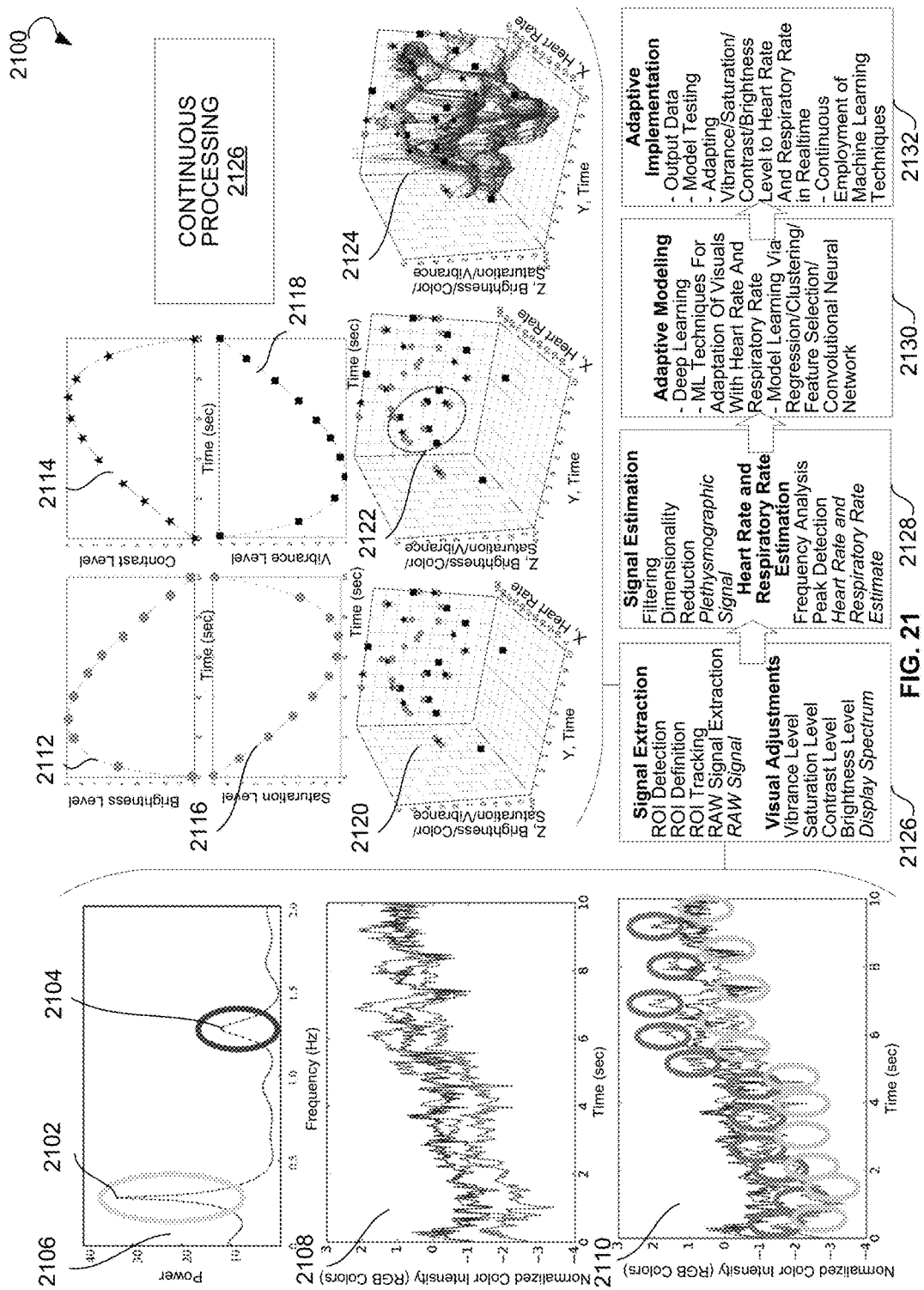
FIG. 21 is a schematic diagram showing an analysis of captured user data by an adaptive interface, according to an example embodiment.

FIG. 21 is a schematic diagram 2100 showing an analysis of captured user data by an adaptive interface, according to an example embodiment. Intensity-based methods 2106, 2108, 2110 can be used to process PPG signals captured by the camera. Normalized color intensity (RGB colors) can be analyzed. Using auto-regressive spectral analysis, two clear peaks can be detected at approximately 0.3 and 1.2 Hz. The peaks correspond to the respiratory rate and the heart rate. The peak 2102 with the frequency of 0.3 Hz corresponds to the respiratory rate, and the peak 2104 with the frequency of 1.2 Hz corresponds to the heart rate. The green channel provides the strongest signal-to-noise ratio. Consequently, the green channel can be used for extracting the heart rate.

Referring back to FIG. 20, upon detecting the red signal 2020, green signal 2022, and blue signal 2024, an average RGB signal can be determined at step 2026. The signal de-trending of the average RGB signal can be performed at step 2028. The processed signal can be normalized at step 2030. Filtering of the normalized signal may be performed at step 2030.

Referring again to FIG. 21, the analysis of captured user data can further include capturing brightness level, contrast level, saturation level, and vibrance level of data shown to the user on the user device. The user perceives the visuals shown on the user device with a continuously changing degree of brightness level, contrast level, saturation level, and vibrance level. The adaptive interface may receive an input in a form of the time of the displaying of the degree or level of brightness, contrast, saturation and vibrance, and the time of the heart rate and respiratory rate as analyzed from user data detected by the camera. As shown in FIG. 21, the inputs are levels of brightness 2112, contrast 2114, saturation 2116, and vibrance 2118 that may be mapped to the time, as well as may be mapped to the time and analysis 2120, 2122, 2124 of values of heart rate and respiratory rate.

The adaptive interface can perform a continuous processing 2126 using a neural processing unit for predictive modeling of the datasets captured by the sensor (the camera) and the visual adjustments. In the adaptive interface, the input of datasets may be processed using deep learning techniques. The deep learning technique may apply specific and differing machine learning techniques to the datasets to learn how to process the datasets and adapt the visual adjustments on the user device to support slower heart rate and respiratory rate. Machine learning techniques can be supervised, semi-supervised, and unsupervised. The adaptive interface may analyze correlations between visual adjustments and heart rate and respiratory rates, process the datasets, and create predictive models to adapt the visual adjustments to the desired outcome of slower heart rate and slower respiratory rate personalized to the user in real-time and continuously. For the inputs, the adaptive interface may identify features of the visual adjustments that are predictive of the outcomes to predict heart rate and respiratory rate. The adaptive interface may use classification, regression, clustering, convolutional neural networks, and other machine learning techniques based on which the datasets are analyzed and the customized output data are predicted for the fastest lowering and slowing of the heart rate and respiratory rate of the user. The probability and predictive modeling performed by the adaptive interface may be adaptive to learn how to adapt the visual adjustments of the user device to the user with varying heart rate and respiratory rate. As the adaptive interface identifies patterns in the datasets of the visual adjustments and heart rate and respiratory rate, the adaptive interface may learn from the observations. When exposed to more observations, the predictive performance of the adaptive interface may be improved.

In an example embodiment, the analysis performed by the adaptive interface may include step 2126, at which signal extraction may be performed. The signal extraction may include detection, definition, and tracking of a region of interest, raw signal extraction to obtain raw signal. The visual adjustments may be selected based on the signal extraction. The visual adjustments may include adjustments of the vibrance level, saturation level, contrast level, brightness level. Based on the visual adjustments, the display spectrum may be determined and applied to a display of the user device.

The analysis may further include step 2128, at which signal estimation may be performed by applying filtering, dimensionality, and reduction to the signal to obtain an RGB signal. Furthermore, the heart rate and respiratory rate may be estimated using frequency analysis and peak detection.

The analysis may further include step 2130, at which adaptive modeling may be performed. The adaptive modeling may include deep learning techniques, machine learning techniques for adaptation of visuals based on the heart rate and respiratory rate, model learning using regression, clustering, feature selection, and convolutional neural networks.

The analysis may further include step 2132, at which adaptive implementation may be performed. Specifically, output data for the user device may be provided, model testing may be performed, levels of vibrance, saturation, contrast, and brightness may be adapted to the heart rate and respiratory rate in real-time and continuously. Machine learning and other techniques may be continuously applied.

Figure 22:
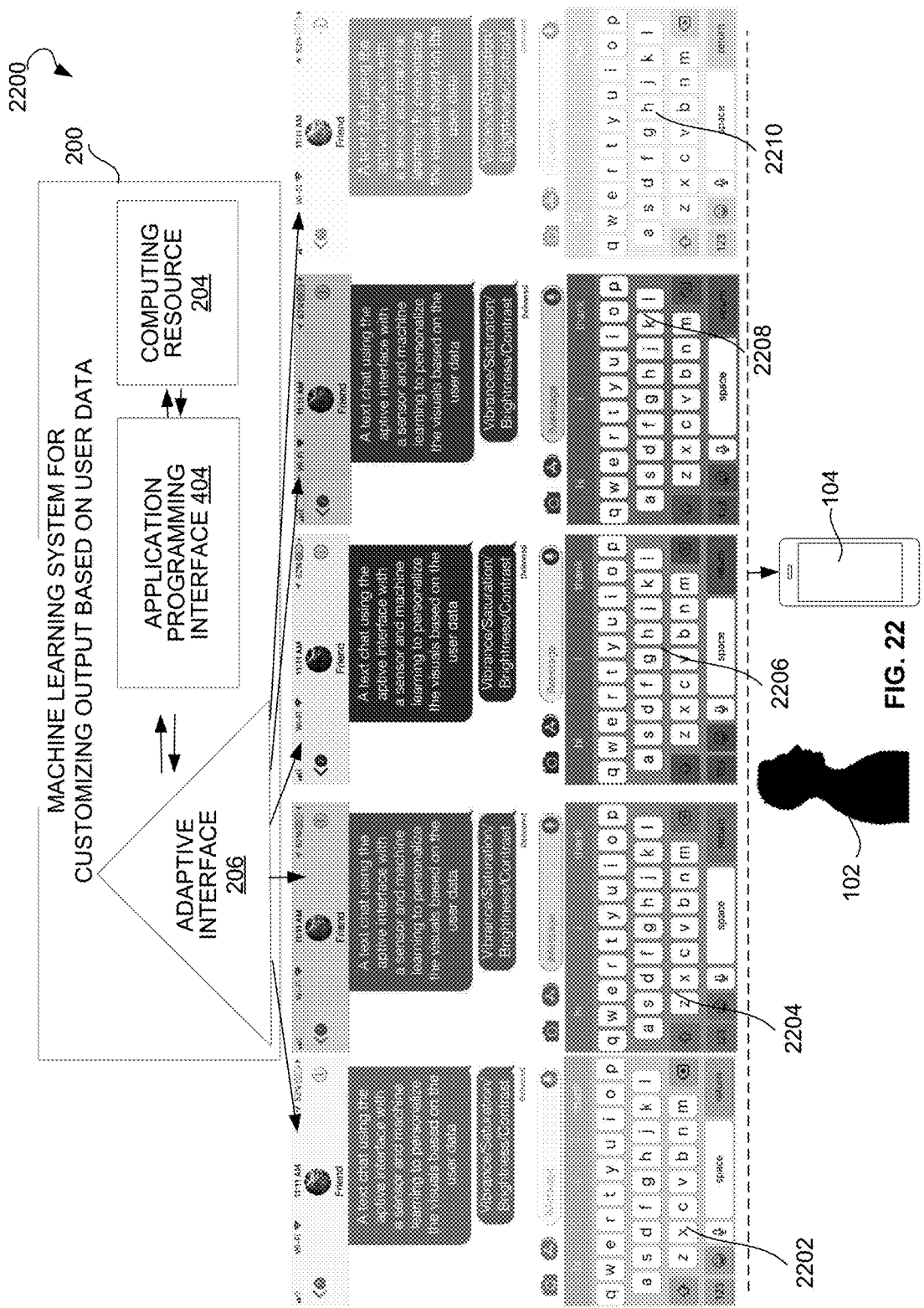
FIG. 22 is a schematic diagram showing output data continuously adapted by an adaptive interface, according to an example embodiment.

FIG. 22 is a schematic diagram 2200 showing output data continuously adapted by an adaptive interface, according to an example embodiment. The adaptive interface 206 may send the analyzed, adapted and customized output data to a CPU or GPU for processing of the personalized datasets. The user 102 may be presented with user interfaces 2202, 2204, 2206, 2208, 2210, which may be continuously personalized in real-time. The user interfaces 2202, 2204, 2206, 2208, 2210 may have varying brightness, contrast, saturation, and vibrance levels. The user device 104 may also provide to the adaptive interface data relating to a processing speed. Therefore, the adaptive interface may learn how to improve the data processing for faster processing so that the visual adjustments for slower heart rate and respiratory rate can be processed faster and more efficiently.

The adaptive interface may receive updates from a network and database about methods to analyze and process the datasets. The updates may be based on scientific studies and tests as to what visuals are supportive to slower the heart rate and the respiratory rate. The updates may also include data on how the heart rate and the respiratory rate can be analyzed and what a "slower" heart rate and respiratory rate means. The focus of the adaptive interface may be to provide a slower, calmer, and deeper heart rate and respiratory rate. The definition of a slower, calmer, and deeper heart rate and respiratory rate can change over time based on scientific and other data, and the adaptive interface may be updated from the network to integrate these changes and adapt the processing of the input data to the updates. Each adaptive interface used by each of a plurality of users may provide data relating to datasets and processing to a database, so the machine learning techniques may use data from a plurality of adaptive interfaces associated with the plurality of users to improve the visual adjustments to the heart rate and respiratory rate of the user. The updates relating to data learned from the plurality of adaptive interfaces and users may be provided to each adaptive interface.

The adaptive interface may be directed to analyzing and evaluating which datasets of visual adjustments, i.e. output data, personalize the visuals shown to the user on the user device to personalize a desired change of heart rate and respiratory rate. The heart rate or respiratory rate can be customized to be lower than the average and/or first detected heart rate and respiratory rate. The adaptive interface may continuously analyze the user data and interaction of the user with the user device and visuals, and may continuously learn to customize the visuals with the visual adjustments to further change the heart rate and respiratory rate of the user.

Figure 23:
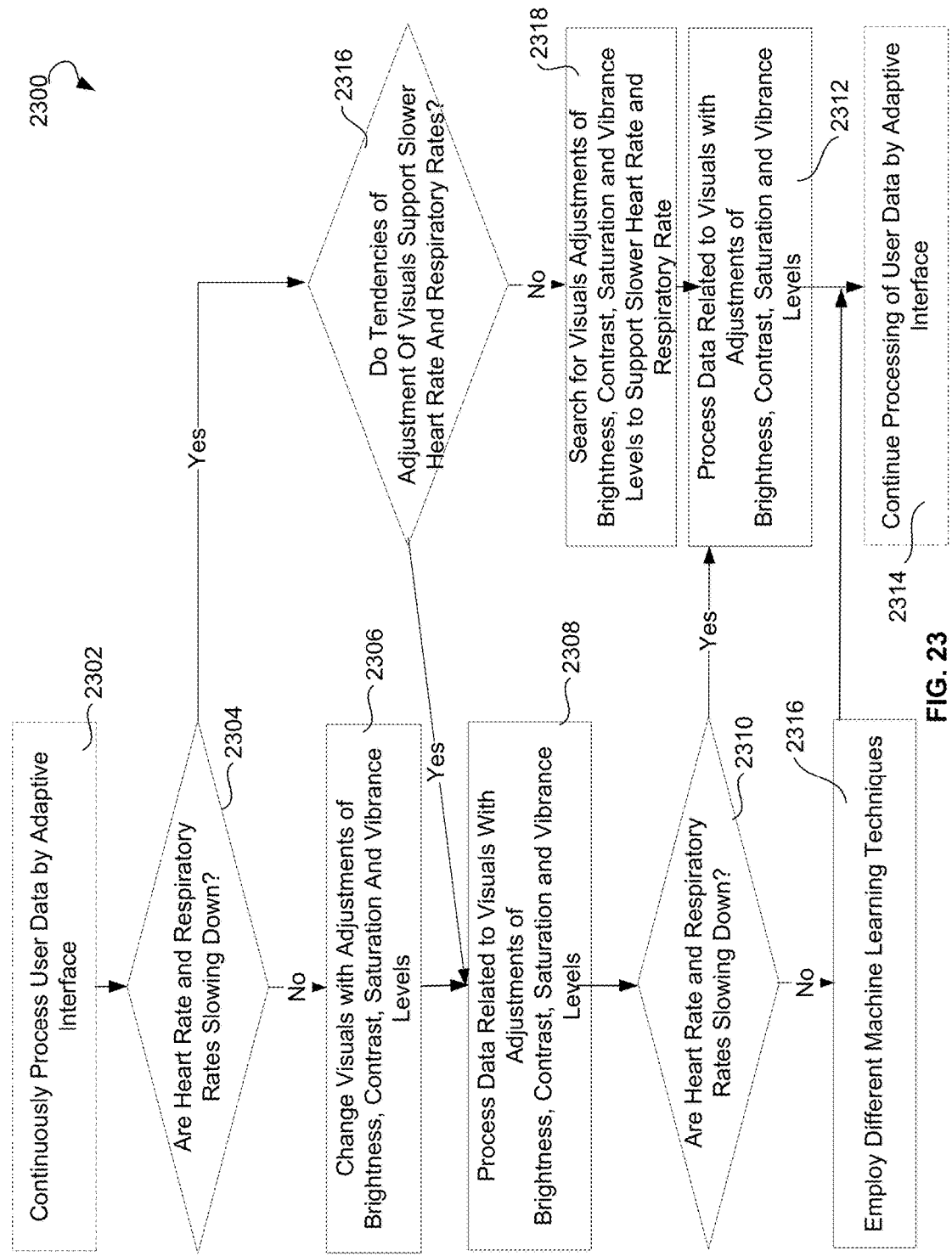
FIG. 23 is a flow chart showing a method for customizing output based on user data, according to an example embodiment.

FIG. 23 is a flow chart 2300 showing a method for customizing output based on user data, according to an example embodiment. The adaptive interface may continuously process user data, as shown by operation 2302. At operation 2304, the adaptive interface may determine whether the heart rate and the respiratory rate of the user slow down. If the heart rate and the respiratory rate do not slow down, the method may continue with operation 2306, at which the adaptive interface may change visuals, i.e., the output data on the user device, using adjustments of brightness level, contrast level, saturation level, and vibrance level of data shown to the user on the user device.

At operation 2308, data related to the changed visuals may be processed and provided to the user on the user device. At operation 2310, the adaptive interface may again determine whether the heart rate and the respiratory rate of the user slow down. If the heart rate and the respiratory rate slow down, the adaptive interface may perform operation 2312, at which data related to the visuals with adjustments of brightness level, contrast level, saturation level, and vibrance level may be processed. At operation 2314, the adaptive interface may continue processing of the user data.

If it is determined at operation 2310 that the heart rate and the respiratory rate do not slow down, the adaptive interface may employ other machine learning techniques at operation 2316 to perform further adaptation of the visuals.

Returning to operation 2304, if it is determined that the heart rate and the respiratory rate slow down, the adaptive interface may determine, at operation 2316, whether tendencies of adjustment of visuals support slower heart rate and respiratory rate. If the tendencies of adjustment of visuals support slower heart rate and respiratory rate, the adaptive interface may continue with operation 2308. If tendencies of adjustment of visuals do not support slower heart rate and respiratory rate, the adaptive interface may perform operation 2318, at which the adaptive interface may search for adjustments of visuals that may support slower heart rate and slower respiratory rate. Upon selecting adjustments of visuals, the adaptive interface may continue with operation 2312.

Figure 24:
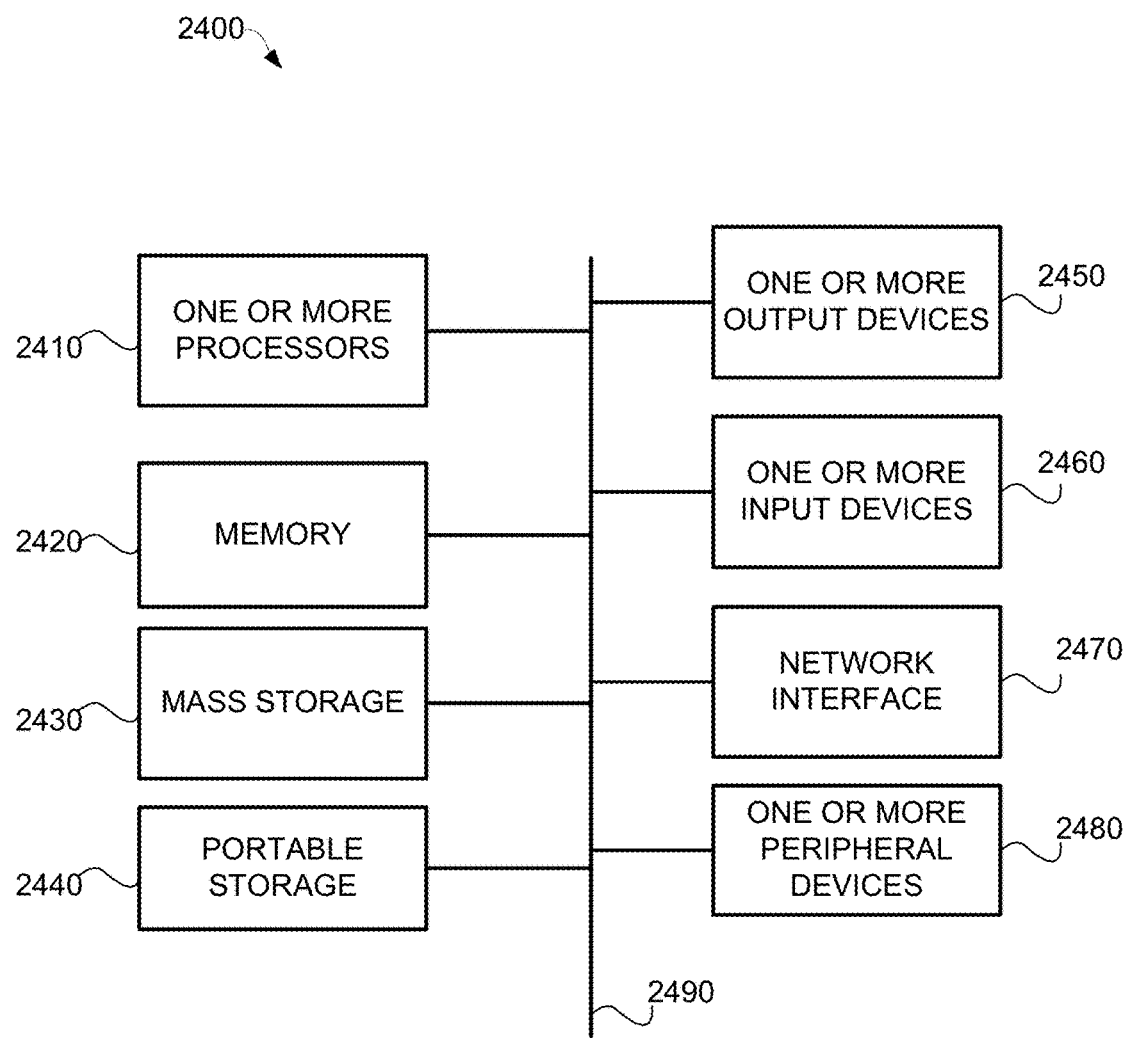
FIG. 24 shows a computing system that can be used to implement a method for customizing output based on user data, according to an example embodiment.

FIG. 24 illustrates an exemplary computing system 2400 that may be used to implement embodiments described herein. The exemplary computing system 2400 of FIG. 24 may include one or more processors 2410 and memory 2420. Memory 2420 may store, in part, instructions and data for execution by the one or more processors 2410. Memory 2420 can store the executable code when the exemplary computing system 2400 is in operation. The exemplary computing system 2400 of FIG. 24 may further include a mass storage 2430, portable storage 2440, one or more output devices 2450, one or more input devices 2460, a network interface 2470, and one or more peripheral devices 2480.

The components shown in FIG. 24 are depicted as being connected via a single bus 2490. The components may be connected through one or more data transport means. The one or more processors 2410 and memory 2420 may be connected via a local microprocessor bus, and the mass storage 2430, one or more peripheral devices 2480, portable storage 2440, and network interface 2470 may be connected via one or more input/output buses.

Mass storage 2430, which may be implemented with a magnetic disk drive or an optical disk drive, is a non-volatile storage device for storing data and instructions for use by a magnetic disk or an optical disk drive, which in turn may be used by one or more processors 2410. Mass storage 2430 can store the system software for implementing embodiments described herein for purposes of loading that software into memory 2420.

Portable storage 2440 may operate in conjunction with a portable non-volatile storage medium, such as a compact disk (CD) or digital video disc (DVD), to input and output data and code to and from the computing system 2400 of FIG. 24. The system software for implementing embodiments described herein may be stored on such a portable medium and input to the computing system 2400 via the portable storage 2440.

One or more input devices 2460 provide a portion of a user interface. The one or more input devices 2460 may include an alphanumeric keypad, such as a keyboard, for inputting alphanumeric and other information, or a pointing device, such as a mouse, a trackball, a stylus, or cursor direction keys. Additionally, the computing system 2400 as shown in FIG. 24 includes one or more output devices 2450. Suitable one or more output devices 2450 include speakers, printers, network interfaces, and monitors.

Network interface 2470 can be utilized to communicate with external devices, external computing devices, servers, and networked systems via one or more communications networks such as one or more wired, wireless, or optical networks including, for example, the Internet, intranet, LAN, WAN, cellular phone networks (e.g., Global System for Mobile communications network, packet switching communications network, circuit switching communications network), Bluetooth radio, and an IEEE 802.11-based radio frequency network, among others. Network interface 2470 may be a network interface card, such as an Ethernet card, optical transceiver, radio frequency transceiver, or any other type of device that can send and receive information. Other examples of such network interfaces may include Bluetooth®, 3G, 4G, and WiFi® radios in mobile computing devices as well as a USB.

One or more peripheral devices 2480 may include any type of computer support device to add additional functionality to the computing system. The one or more peripheral devices 2480 may include a modem or a router.

The components contained in the exemplary computing system 2400 of FIG. 24 are those typically found in computing systems that may be suitable for use with embodiments described herein and are intended to represent a broad category of such computer components that are well known in the art. Thus, the exemplary computing system 2400 of FIG. 24 can be a personal computer, hand held computing device, telephone, mobile computing device, workstation, server, minicomputer, mainframe computer, or any other computing device. The computer can also include different bus configurations, networked platforms, multi-processor platforms, and so forth. Various operating systems (OS) can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the example embodiments. Those skilled in the art are familiar with instructions, processor(s), and storage media.

It is noteworthy that any hardware platform suitable for performing the processing described herein is suitable for use with the example embodiments. The terms "computer-readable storage medium" and "computer-readable storage media" as used herein refer to any medium or media that participate in providing instructions to a CPU for execution. Such media can take many forms, including, but not limited to, non-volatile media, volatile media, and transmission media. Non-volatile media include, for example, optical or magnetic disks, such as a fixed disk. Volatile media include dynamic memory, such as RAM. Transmission media include coaxial cables, copper wire, and fiber optics, among others, including the wires that include one embodiment of a bus. Transmission media can also take the form of acoustic or light waves, such as those generated during radio frequency and infrared data communications. Common forms of computer-readable media include, for example, a floppy disk, a flexible disk, a hard disk, magnetic tape, any other magnetic medium, a CD-read-only memory (ROM) disk, DVD, any other optical medium, any other physical medium with patterns of marks or holes, a RAM, a PROM, an EPROM, an EEPROM, a FLASHEPROM, any other memory chip or cartridge, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Thus, machine learning systems and methods for customizing output based on user data are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A machine learning system for customizing output based on user data, the system comprising:
   at least one sensor configured to continuously capture the user data associated with a user during perception of output data by the user;
   at least one computing resource comprising a first processor and a first memory, the at least one computing resource being configured to:
      analyze the user data received from the at least one sensor; and
      based on the analysis, determine dependencies between the user data and the output data; and
   an adaptive interface comprising a second processor and a second memory, the adaptive interface being configured to continuously customize the output data using at least one machine learning technique based on the analysis of the user data and the dependencies, the customized output data intended to elicit an automatic and immediate personalized change of a biological response of the user to perception of the customized output data by the user without requiring the user to take an action in response to the customized output data.

2. The system of claim 1, wherein the user data includes at least one of the following: biological data of a user, biological data of a plurality of users, historical data of the user, historical data of the plurality of users, and ambient data.

3. The system of claim 2, wherein the automatic and immediate personalized change includes a change in the biological data.

4. The system of claim 2, wherein the biological data includes at least one of the following: a respiratory rate, a heart rate, a heart rate variability, an electroencephalography, an electrocardiography, an electromyography, an electrodermal activity, a mechanomyography, a haptic interaction, a motion, a gesture, pupil movement, a biological analyte, a biological structure, a microorganism, a color of skin of the user, a blood glucose level, blood oxygenation, and blood pressure.

5. The system of claim 2, wherein the ambient data is associated with at least one of the following: light, heat, motion, moisture, and pressure.

6. They system of claim 1, wherein the at least one sensor includes a biological sensor.

7. The system of claim 1, wherein the customized output data includes at least one of an audio output and a graphics output.

8. The system of claim 1, wherein the at least one computing resource includes at least one of the following: an application programming interface, a server, a cloud computing resource, a database, a network, and a blockchain.

9. The system of claim 1, wherein the at least one computing resource includes one of the following: a smartphone, a tablet computer, a phablet computer, a laptop computer, a desktop computer, an augmented reality device, a virtual reality device, a mixed reality device, a retinal implant, an artificial olfaction device, headphones, and an audio output device.

10. The system of claim 1, wherein the at least one computing resource includes one of a central processing unit, a graphics processing unit, and a neural processing unit.

11. The system of claim 1, wherein the at least one sensor is affixed to a user.

12. The system of claim 1, wherein the at least one sensor includes at least one of the following: a thermal imaging camera, a digital camera, a breath sensor, a depth sensor, a radar sensor, and a gyroscope.

13. The system of claim 1, wherein the at least one machine learning technique includes one or more of the following: an artificial neural network, a convolutional neural network, a Bayesian neural network, a supervised machine learning algorithm, a semi-supervised machine learning algorithm, an unsupervised machine learning algorithm, and a reinforcement learning.

14. The system of claim 1, wherein the automatic and immediate personalized change in the user data includes at least one of the following: a change of perception time, a change of a respiratory rate, a change of a breathing rate, a change of a heart rate, a change of a heart rate variability, a change of a haptic interaction, a change of an electroencephalographic signal, a change of an electrocardiographic signal, a change of an electromyographic signal, a change of a mechanomyographic signal, a change of an electrodermal activity, a change of a motion, a change of a gesture, a change of a pupil movement, a change of a biological structure, a change of a microorganism, a change of a color of skin of the user, a change of blood glucose levels, a change of a blood oxygenation, a change of a blood pressure, a change of a biological analyte, and change of a stress level.

15. A method for customizing an output based on user data, the method comprising:
continuously capturing, by at least one sensor, the user data associated with a user during perception of output data by the user;
analyzing, by at least one computing resource comprising a first processor and a first memory, the user data received from the at least one sensor;
based on the analysis, determining dependencies between the user data and the output data; and
continuously customizing, by an adaptive interface comprising a second processor and a second memory, the output data using at least one machine learning technique based on the analysis of the user data and the dependencies, the customized output data intended to elicit an automatic and immediate personalized change of a biological response of the user to perception of the customized output data by the user without requiring the user to take an action in response to the customized output data.

16. The method of claim 15, further comprising:
aggregating, by the at least one computing resource, further user data associated with a plurality of users into federated user data;
analyzing, by the at least one computing resource, the federated user data using collaborative machine learning; and
adapting, by the at least one computing resource, the at least one machine learning technique for individual users based on the results of the analysis of the federated user data.

17. The method of claim 15, further comprising:
continuously adapting, by the adaptive interface, a media output based on user interactions with the adaptive interface.

18. The method of claim 15, wherein the at least one sensor includes a device for analyzing electronic signals emitted by a user, wherein the method further comprises extracting, by the device, one of a physiological parameter of the user and an activity associated with the user.

19. The method of claim 15, wherein the continuous customizing of the output data includes at least one of the following: changing a color, playing audio-perceived stimuli, providing a haptic feedback, changing a font, changing a shape of the font, changing a brightness, changing a contrast, changing an illuminance, changing a warmth, changing a saturation, changing a fade, changing a shadow, changing a sharpness, changing a structure, generating computer images, changing a bass, changing a volume, changing a pitch of a sound, changing a treble, changing a balance, changing a graphical user interface, and changing a user experience design.

20. A machine learning system for customizing output based on user data, the system comprising:
at least one sensor configured to continuously capture the user data associated with a user during perception of output data by the user;
at least one computing resource comprising a first processor and a first memory, the at least one computing resource being configured to:
analyze the user data received from the at least one sensor;
based on the analysis, determine dependencies between the user data and the output data; and
aggregate further user data associated with a plurality of users into federated user data;
analyze the federated user data using collaborative machine learning; and
adapt the at least one machine learning technique for individual users based on the results of the analysis of the federated user data; and
an adaptive interface comprising a second processor and a second memory, the adaptive interface being configured to:
continuously customize the output data using at least one machine learning technique based on the analysis of the user data and the dependencies, the customized output data intended to elicit an automatic and immediate personalized change of a biological response of the user to perception of the customized output data by the user without requiring the user to take an action in response to the customized output data; and
continuously adapt a media output based on user interactions with the adaptive interface.

* * * * *